US007592335B2

(12) United States Patent
Das et al.

(10) Patent No.: US 7,592,335 B2
(45) Date of Patent: Sep. 22, 2009

(54) OXAZOLIDINONE DERIVATIVES AS ANTIMICROBIALS

(75) Inventors: Biswajit Das, Haryana (IN); Sonali Rudra, Haryana (IN); Sangita Sangita, Allahabad (IN); Mohammad Salman, Princeton, NJ (US); Ashok Rattan, Haryana (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

(21) Appl. No.: 11/911,576

(22) PCT Filed: Apr. 12, 2006

(86) PCT No.: PCT/IB2006/000871

§ 371 (c)(1),
(2), (4) Date: Apr. 10, 2008

(87) PCT Pub. No.: WO2006/109156

PCT Pub. Date: Oct. 19, 2006

(65) Prior Publication Data

US 2008/0188470 A1    Aug. 7, 2008

(30) Foreign Application Priority Data

Apr. 15, 2005   (IN) ......................... 951/05

(51) Int. Cl.
C07D 498/04   (2006.01)
A61K 31/5383   (2006.01)
(52) U.S. Cl. .................. 514/230.5; 544/105
(58) Field of Classification Search ............. 544/105; 514/230.5
See application file for complete search history.

(56) References Cited

U.S. PATENT DOCUMENTS

| 3,536,809 | A | 10/1970 | Applezweig ............ 424/28 |
| 3,598,123 | A | 8/1971 | Zaffaroni ............ 128/268 |
| 3,845,770 | A | 11/1974 | Theeuwes et al. ........ 128/260 |
| 3,916,899 | A | 11/1975 | Theeuwes et al. ........ 128/260 |
| 4,008,719 | A | 2/1977 | Theeuwes et al. ........ 128/260 |
| 5,565,571 | A | 10/1996 | Barbachyn et al. ........ 546/144 |
| 5,654,428 | A | 8/1997 | Barbachyn et al. ........ 544/235 |
| 5,654,435 | A | 8/1997 | Barbachyn et al. ....... 546/271.4 |
| 5,756,732 | A | 5/1998 | Barbachyn et al. ........ 544/112 |
| 5,801,246 | A | 9/1998 | Barbachyn et al. ........ 548/152 |
| 6,255,304 | B1 | 7/2001 | Hester, Jr. et al. ........ 514/227.8 |
| 6,689,779 | B2 | 2/2004 | Lee et al. ............... 514/235.8 |
| 2004/0102494 | A1 | 5/2004 | Selvakumar et al. |

FOREIGN PATENT DOCUMENTS

| DE | 42 00 415 | 7/1993 |
| WO | WO 93/09103 | 5/1993 |
| WO | WO 93/23384 | 11/1993 |
| WO | WO 98/54161 | 12/1998 |
| WO | WO 00/29396 | 5/2000 |
| WO | WO 01/80841 | 11/2001 |
| WO | WO 01/94342 | 12/2001 |
| WO | WO 03/006447 | 1/2003 |
| WO | WO 03/007870 | 1/2003 |
| WO | WO 03/008389 | 1/2003 |
| WO | WO 03/022824 | 3/2003 |
| WO | WO 03/072553 | 9/2003 |
| WO | WO 03/097059 | 11/2003 |
| WO | WO 2004/014392 | 2/2004 |
| WO | WO 2004/056818 | 7/2004 |
| WO | WO 2004/089944 | 10/2004 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Wolff Manfred E. "Burger's Medicinal Chemistry, 5ed, Part 1" John Wiley & Sons, 1995, pp. 975-977.*
Banker, G.S. et al, "Modern Paharmaceutices, 3ed." Marcel Dekker, New York, 1996, pp. 451 and 596.*
Greene, T.Q. and Wuts, P.G.M., 1991. *Protective Groups in Organic Synthesis*. 2nd Edition. New York: Wiley Interscience Publications.
Graβmann et al., "Progress in the proxifan class: heterocyclic congeners as novel potent and selective histamine $H_3$-receptor antagonists", *European Journal of Pharmaceutical Sciences*, 15:367-378 (2002).
Genin et al., "Substituent Effects on the Antibacterial Activity of Nitrogen-Carbon-Linked (Azolylphenyl)oxazolidinones with Expanded Activity Against the Fastidious Gram-Negative Organisms *Haemophilus influenzae* and *Moraxella catarrhalis*", *Journal of Medicinal Chemistry*, 43(5):953-970 (2000).
Rao and Reddy, "Formation & Pyrolysis of 1-(2'-Pyridyl) -5-aryltetrazoles", *Indian Journal of Chemistry*, 22B:117-120 (1983).

(Continued)

*Primary Examiner*—Kahsay T Habte
(74) *Attorney, Agent, or Firm*—James J. DeYonker, Esq.

(57) ABSTRACT

Provided herein are novel substituted phenyl oxazolidinones and to processes for the synthesis thereof. Also provided are pharmaceutical compositions comprising one or more compounds described herein The compounds described can be useful antimicrobial agents, which can be effective against a number of human and veterinary pathogens, including gram-positive aerobic bacteria such as multiple-resistant staphylococci, streptococci and enterococci, as well as, anaerobic organisms, such as *Bacterioides* spp. and *Clostridia* spp. species, and acid fast organisms, such as *Mycobacterium tuberculosis, Mycobacterium avium* and *Mycobacterium* spp.

8 Claims, No Drawings

OTHER PUBLICATIONS

Chambers et al., "Identification of a Novel, Selective $GABA_A$ α5 Receptor Inverse Agonist Which Enhances Cognition", *Journal of Medicinal Chemistry*, 46(11):2227-2240 (2003).

Chauviére et al., "Nucleophilic Substitution Studies on Nitroimidazoles, and Applications to the Synthesis of Biologically Active Compounds", *Journal of Heterocyclic Chemistry*, 37:119-126 (2000).

Markevitch et al., "An Efficient Synthesis of 5-Bromopyridine-2-carbonitrile", *Synthetic Communications*, 33(19):3285-3289 (2003).

Barbachyn et al., "Identification of Phenylisoxazolines as Novel and Viable Antibacterial Agents Active against Gram-Positive Pathogens", *Journal of Medicinal Chemistry*, 46(2):284-302 (2003).

NCCLS. *Methods for Dilution Antimicrobial Susceptibility Tests for Bacteria That Grow Aerobically; Approved Standard—Fifth Edition*. NCCLS document M7-A5. NCCLS, Pennsylvania USA, 2000.

NCCLS. *Performance Standards for Antimicrobial Susceptibility Testing; Twelfth Informational Supplement*. NCCLS document M100-S12 [ISBN 1-56238-454-6]. NCCLS, Pennsylvania USA, 2002.

"Linezolid, Oxazolidinone Antibacterial" Drugs of the Future, Barcelona ES, 21(11), pp. 116-1123, (1996).

Zurenko, et al., "Oxazolidinone Antibacterial Agents: Development of the Clinical Candidates Eperezolid and Linezolid" Expert Opinion on Investigational Drugs, Ashley Publications Ltd., London GB 6(2), pp. 151-158, (1997).

* cited by examiner

OXAZOLIDINONE DERIVATIVES AS ANTIMICROBIALS

FIELD OF THE INVENTION

Provided herein are novel substituted phenyl oxazolidinones and to processes for the synthesis thereof. Also provided are pharmaceutical compositions comprising one or more compounds described herein The compounds described can be useful antimicrobial agents, which can be effective against a number of human and veterinary pathogens, including gram-positive aerobic bacteria such as multiple-resistant staphylococci, streptococci and enterococci, as well as, anaerobic organisms, such as *Bacterioides* spp. and *Clostridia* spp. species, and acid fast organisms, such as *Mycobacterium tuberculosis, Mycobacterium avium* and *Mycobacterium* spp.

BACKGROUND OF THE INVENTION

Increasing antibacterial resistance in Gram-positive bacteria has presented a formidable treatment problem. The enterococci, although traditionally no virulent pathogens, have been shown, when associated with Vancomycin resistance, to have an attributable mortality of approximately 40%. *Staphylococcus aureus*, the traditional pathogen of postoperative wounds, has been resistant to Penicillin due to production of penicillinases. This resistance was overcome by the development of various penicillinase stable β-lactams. But the pathogen responded by synthesizing modified target penicillin binding protein-2' leading to less affinity for β-lactam antibiotics and a phenotype known as Methicillin Resistant *S. aureus* (MRSA). These strains, until recently were susceptible to Vancomycin, which in spite of its various drawbacks, has become the drug of choice for MRSA infections. *Streptococcus pneumoniae* is a major pathogen causing pneumonia, sinusitis and meningitis. Until very recently it was highly susceptible to penicillin. Recently though, different PBP 2' strains with different susceptibility to penicillin have been reported from across the globe. Oxazolidinones are a new class of synthetic antimicrobial agents, which kill gram-positive pathogens by inhibiting a very early stage of protein synthesis. Oxazolidinones inhibit the formation of ribosomal initiation complex involving 30S and 50S ribosomes leading to prevention of initiation complex formation. Due to their novel mechanism of action, these compounds are active against pathogens resistant to other clinically useful antibiotics.

Various oxazolidinone derivatives have been disclosed and reportedly having antibacterial activity. However in view of the above, there remains a need for novel substituted phenyloxazolidinones, which in particular can be effective antibacterial agents.

SUMMARY OF THE INVENTION

Provided herein are novel phenyloxazolidinones derivatives that exhibit antibacterial activity, than available with the present compounds against gram positive pathogens, for example, methicilline resistant *Staphylococcus aureus* (MRSA), Vancomycin-resistant Enterococci (VRE) and penicillin-resistant *Streptococcus pneumoniae* (PRSP), multiple drug-resistant tuberculosis (MDR-TB) and MAI sirens; and gram negative pathogens, for example, morazella catarrhalis and haemophilus influenza, to provide safe and effective treatment of bacterial infection.

Also provided are the to synthesis, identification and profile of phenyloxazolidinone derivatives, which can be used as active agents against, multiple resistant gram-positive pathogens, for example, MRSA, VRE—*Streptococcus pneumonia* and others.

In one aspect, provided herein is a compound of Formula I,

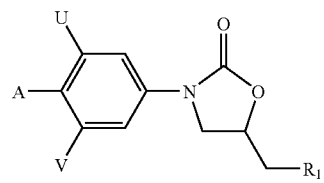

Formula I and their pharmaceutically acceptable salts, pharmaceutically acceptable solvates, esters, enantiomers, diastereomers, N-oxides, polymorphs, prodrugs or metabolites, wherein
U and V can be selected from hydrogen and fluorine (wherein both U and V cannot simultaneously be hydrogen);
A is selected from

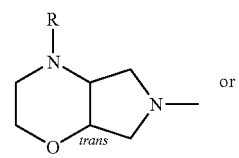

Formula A

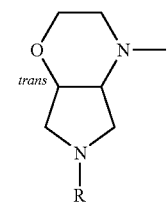

Formula B

R is H, alkyl, alkenyl, alkynyl, alkoxy, cycloalkyl, aryl, aralkyl, heteroaryl, heterocyclyl, heteroarylalkyl or heterocyclylalkyl, —COR$_a$, —C(O)OR$_a$, and S(O)$_2$R$_a$;
R$_1$ is azido, halogen, NCS, NHYR$_j$NR$_j$C(=T)NR$_j$R$_q$, NR$_j$R$_q$ or NR$_j$(C=O)OR$_s$( );
R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;
Y is (C=O), (C=S) or SO$_2$;
R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;
T is O, S, —N(CN), —N(NO$_2$), —CH(NO$_2$);
R$_j$ is hydrogen, alkyl, alkenyl, cycloalkyl, aryl, aralkyl, heterocyclyl, heteroaryl, heteroarylalkyl or heterocyclylalkyl;
R$_q$ is hydrogen, alkyl, cycloalkyl, aryl, aralkyl, heteroaryl, heterocyclyl, heteroarylalkyl or heterocyclylalkyl, and
R$_s$ is alkyl, alkenyl, alkynyl, cycloalkyl, aryl, aralkyl, heteroarylalkyl or heterocyclylalkyl.1

In another aspect, provided are compounds selected from:
3-{3-fluoro-4-[(7aE)-hexahydropyrrolo[3,4-b][1,4]oxazin-4 (4aH)-yl]phenyl}-5-(iodomethyl)-1,3-oxazolidin-2-one (Compound No. 01);
tert-butyl (7aE)-6-{2-fluoro-4-[5-(iodomethyl)-2-oxo-1,3-oxazolidin-3-yl]phenyl}hexahydropyrrolo[3,4-b][1,4]oxazine-4(4aH)-carboxylate (Compound No. 02);

tert-butyl (7aE)-6-{4-[5-(aminomethyl)-2-oxo-1,3-oxazolidin-3-yl]-2-fluorophenyl}hexahydropyrrolo[3,4-b][1,4]oxazine-4(4aH)-carboxylate (Compound No. 03);

tert-butyl (7aE)-6-(4-{5-[(acetylamino)methyl]-2-oxo-1,3-oxazolidin-3-yl}-2-fluorophenyl)hexahydropyrrolo[3,4-b][1,4]oxazine-4(4aH)-carboxylate (Compound No. 04);

N-[(3-{3-fluoro-4-[(7aE)-hexahydropyrrolo[3,4-b][1,4]oxazin-6(2H)-yl]phenyl}-2-oxo-1,3-oxazolidin-5-yl)methyl]acetamide (Compound No. 05);

2-[(7aE)-6-(4-{5-[(acetylamino)methyl]-2-oxo-1,3-oxazolidin-3-yl}-2-fluorophenyl)hexahydropyrrolo[3,4-b][1,4]oxazin-4(4aH)-yl]-2-oxoethyl acetate (Compound No. 06);

N-[(3-{4-[(7aE)-4-acetylhexahydropyrrolo[3,4-b][1,4]oxazin-6(2H)-yl]-3-fluorophenyl}-2-oxo-1,3-oxazolidin-5-yl)methyl]acetamide (Compound No. 07);

N-[(3-{4-[(7aE)-4-benzoylhexahydropyrrolo[3,4-b][1,4]oxazin-6(2H)-yl]-3-fluorophenyl}-2-oxo-1,3-oxazolidin-5-yl)methyl]acetamide (Compound No. 08);

N-[(3-{3-fluoro-4-[(7aE)-4-(4-fluorobenzoyl)hexahydropyrrolo[3,4-b][1,4]oxazin-6(2H)-yl]phenyl}-2-oxo-1,3-oxazolidin-5-yl)methyl]acetamide (Compound No. 09);

N-[(3-{3-fluoro-4-[(7aE)-4-(methylsulfonyl)hexahydropyrrolo[3,4-b][1,4]oxazin-6(2H)-yl]phenyl}-2-oxo-1,3-oxazolidin-5-yl)methyl]acetamide (Compound No. 10);

N-[(3-{3-fluoro-4-[(7aE)-4-glycoloylhexahydropyrrolo[3,4-b][1,4]oxazin-6(2H)-yl]phenyl}-2-oxo-1,3-oxazolidin-5-yl)methyl]acetamide (Compound No. 11);

3-{3-fluoro-4-[(7aE)-hexahydropyrrolo[3,4-b][1,4]oxazin-4(4aH)-yl]phenyl}-5-(iodomethyl)-1,3-oxazolidin-2-one (Compound No. 12);

N-[(3-{3-fluoro-4-[(7aE)-hexahydropyrrolo[3,4-b][1,4]oxazin-4(4aH)-yl]phenyl}-2-oxo-1,3-oxazolidin-5-yl)methyl]acetamide (Compound No. 13);

tert-butyl (7aE)-4-{2-fluoro-4-[5-(iodomethyl)-2-oxo-1,3-oxazolidin-3-yl]phenyl}hexahydropyrrolo[3,4-b][1,4]oxazine-6(2H)-carboxylate (Compound No. 14);

tert-butyl (7aE)-4-(4-{5-[(acetylamino)methyl]-2-oxo-1,3-oxazolidin-3-yl}-2-fluorophenyl)hexahydropyrrolo[3,4-b][1,4]oxazine-6(2H)-carboxylate (Compound No. 15);

2-[(7aE)-4-(4-{5-[(acetylamino)methyl]-2-oxo-1,3-oxazolidin-3-yl}-2-fluorophenyl)hexahydropyrrolo[3,4-b][1,4]oxazin-6(2H)-yl]-2-oxoethyl acetate (Compound No. 16);

N-[(3-{4-[(7aE)-6-benzoylhexahydropyrrolo[3,4-b][1,4]oxazin-4(4aH)-yl]-3-fluorophenyl}-2-oxo-1,3-oxazolidin-5-yl)methyl]acetamide (Compound No. 17);

N-[(3-{4-[(7aE)-6-acetylhexahydropyrrolo[3,4-b][1,4]oxazin-4(4aH)-yl]-3-fluorophenyl}-2-oxo-1,3-oxazolidin-5-yl)methyl]acetamide (Compound No. 18);

N-[(3-{3-fluoro-4-[(7aE)-6-(methylsulfonyl)hexahydropyrrolo[3,4-b][1,4]oxazin-4(4aH)-yl]phenyl}-2-oxo-1,3-oxazolidin-5-yl)methyl]acetamide (Compound No. 19); or N-[(3-{3-fluoro-4-[(7aE)-6-glycoloylhexahydropyrrolo[3,4-b][1,4]oxazin-4(4aH)-yl]phenyl}-2-oxo-1,3-oxazolidin-5-yl)methyl]acetamide (Compound No. 20).

In yet another aspect, provided are pharmaceutical compositions comprising a therapeutically effective amount of a compound of Formula I

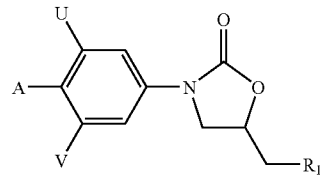

Formula I or its pharmaceutically acceptable salts, pharmaceutically acceptable solvates, enantiomers, diastereomers or polymorphs, and one or more pharmaceutically acceptable carriers, wherein U, V, $R_1$ and A are the same as defined herein.

In another aspect, provided are methods of treating or preventing microbial infections in a mammal comprising administering to a mammal in need thereof a therapeutically effective amount of a compound of Formula I

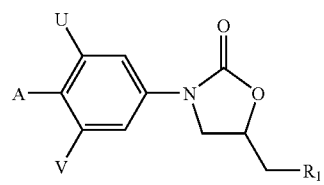

Formula I or its pharmaceutically acceptable salts, pharmaceutically acceptable solvates, enantiomers, diastereomers or polymorphs, wherein U, V, $R_1$ and A are the same as defined herein.

The methods can include one or more of the following embodiments. For example, the microbial infections can be caused by gram-positive and gram-negative bacteria. In another embodiment, the gram-positive bacteria can be selected from *Staphylococcus* spp., *Streptococcus* spp., *Bacillus* spp., *Corynebacterum* spp., *Clostridia* spp., *Peptostreptococcus* spp., *Listeria* spp. or *Legionella* spp.

In yet another aspect, provided are methods of treating or preventing aerobic and anaerobic bacterial infections in a mammal comprising administering to mammal in need thereof a therapeutically effective amount of a compound of Formula I

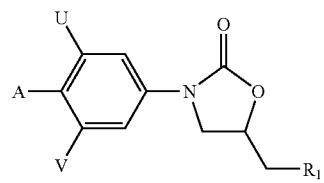

Formula I or its pharmaceutically acceptable salts, pharmaceutically acceptable solvates, enantiomers, diastereomers or polymorphs, wherein U, V, $R_1$, and A are the same as defined herein.

DETAILED DESCRIPTION OF THE INVENTION

Provided herein are compounds of Formula I

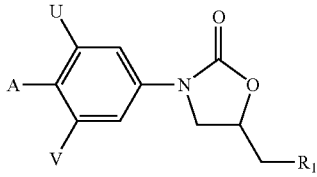

Formula I and their pharmaceutically acceptable salts, pharmaceutically acceptable solvates, esters, enantiomers, diastereomers, N-oxides, polymorphs, pro drugs or metabolites, wherein
U and V can be selected from hydrogen and fluorine (wherein both U and V cannot simultaneously be hydrogen);
A is selected from

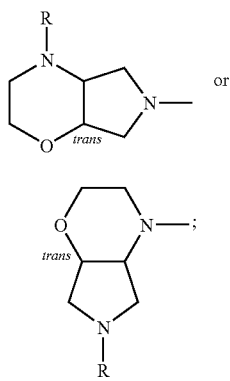

Formula A or

Formula B

R is H, alkyl, alkenyl, alkynyl, alkoxy, cycloalkyl, aryl, aralkyl, heteroaryl, heterocyclyl, heteroarylalkyl or heterocyclylalkyl, —COR$_a$, —C(O)OR$_a$, and S(O)$_2$R$_a$;

R$_1$ is azido, halogen, NCS, NHYR$_j$NR$_j$C(=T)NR$_j$R$_q$, NR$_j$R$_q$ or NR$_j$(C=O)OR$_s$( );

R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or SO$_2$;

R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —N(NO$_2$), —CH(NO$_2$);

R$_j$ is hydrogen, alkyl, alkenyl, cycloalkyl, aryl, aralkyl, heterocyclyl, heteroaryl, heteroarylalkyl or heterocyclylalkyl;

R$_q$ is hydrogen, alkyl, cycloalkyl, aryl, aralkyl, heteroaryl, heterocyclyl, heteroarylalkyl or heterocyclylalkyl, and R$_s$ is alkyl, alkenyl, alkynyl, cycloalkyl, aryl, aralkyl, heteroarylalkyl or heterocyclylalkyl.

Also provided are processes for synthesizing novel phenyloxazolidinone derivatives of Formula I

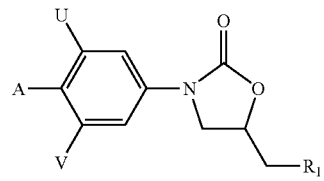

Formula I and their pharmaceutically acceptable salts, pharmaceutically acceptable solvates, esters, enantiomers, diastereomers, N-oxides, polymorphs, prodrugs or metabolites, wherein
U and V can be selected from hydrogen and fluorine (wherein both U and V cannot simultaneously be hydrogen);
A is selected from;

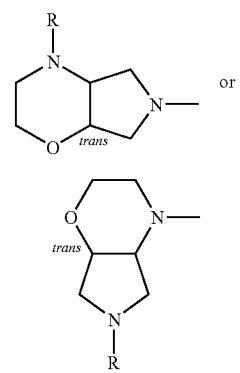

Formula A or

Formula B

R is H, alkyl, alkenyl, alkynyl, alkoxy, cycloakyl, aryl, aralkyl, heteroaryl, heterocyclyl, heteroarylalkyl or heterocyclylalkyl, —COR$_a$, —C(O)OR$_a$, and S(O)$_2$R$_a$;

R$_1$ is azido, halogen, NCS, NHYR$_j$NR$_j$C(=T)NR$_j$R$_q$, NR$_j$R$_q$ or NR$_j$(C=O)OR$_s$( );

R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or SO$_2$;

R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —N(NO$_2$), —CH(NO$_2$);

R$_j$ is hydrogen, alkyl, alkenyl, cycloalkyl, aryl, aralkyl, heterocyclyl, heteroaryl, heteroarylalkyl or heterocyclylalkyl;

R$_q$ is hydrogen, alkyl, cycloalkyl, aryl, aralkyl, heteroaryl, heterocyclyl, heteroarylalkyl or heterocyclylalkyl, and R$_s$ is alkyl, alkenyl, alkynyl, cycloalkyl, aryl, aralkyl, heteroarylalkyl or heterocyclylalkyl.

Compounds described herein can be useful antimicrobial agents, and in particular effective against a number of human and veterinary pathogens, including aerobic and Gram-positive bacteria, for example, multiply-antibiotic resistant staphylococci and streptococci, as well as anaerobic organisms for example, *Mycobacterium tuberculosis* and other *mycobacterium* species.

Pharmaceutical compositions for use in the methods described herein may be prepared by any of the methods of pharmacy, but all methods include the step of bringing into association the active ingredient with the carrier which constitutes one or more necessary ingredients. In general, the compositions are prepared by uniformly and intimately admixing the active ingredient with pharmaceutically acceptable liquid carriers or finely divided solid carriers or both, and then, if necessary, shaping the product into the desired presentation.

Solid form preparations include powders, tablets, pills, dispersible granules, dragees, capsules, cachets, suppositories, troches, patches, gel caps, magmas, lozenges, creams, pastes, plasters, lotions, discs, or ointments. Liquid form preparations include solutions, suspensions, emulsions, microemulsions, syrups, elixirs, aerosols, nasal spays or oral sprays.

Solid carriers can include one or more substances, which may also act as diluents, flavoring agents, solubilizers, lubricants, suspending agents, binders, or disintegrating agents. Solid carriers can also include finely divided solids, which can be in admixture with one or more finely divided compounds described herein.

In preparing tablets, one or more compounds described herein can be mixed with one or more carriers having the necessary binding properties in suitable proportions and compacted into the desired shape and size. In some embodiments, powders and tablets can contain from about 5 to about 70 percent of one or more compounds described herein. Suitable solid carriers include, for example, sucrose, glucose, lactose, pectin, mannitol, silicic acid, dextrin, starch, gelatin, tragacanth, low melting wax, cocoa butter sugars, sodium citrate, dicalcium phosphate, microcrystalline cellulose, granulating agents, lubricants, binders, disintegrating agents, absorption accelerators, wetting agents, adsorbents and the like. Binders include, for example, carboxymethylcellulose, alginates, gelatins, polyvinylpyrrolidinone, sucrose, and acacia. Disintegrating agents include, for example, agar-agar, calcium carbonate, potato starch, alginic acid, certain silicates and sodium carbonate. Absorption accelerators include, for example, quaternary ammonium compounds; wetting agents include, for example, cetyl alcohol, and glycerol mono stearate. Adsorbents include, for example, Kaolin. Lubricants include, for example, talc, calcium stearate, magnesium stearate, solid polyethyleneglycol, sodium lauryl sulphate and mixtures thereof. In the case of capsules, tablets, pills, the dosage form may also comprise buffering agents. For example, a tablet may be prepared by compression or molding, optionally, with one or more accessory ingredients. Compressed tablets may be prepared by compressing in a suitable machine the active ingredient in a free-flowing form such as powder or granules, optionally mixed with one or more binders, lubricants, inert diluents, surface active or dispersing agents. Molded tablets may be made by molding, in a suitable machine, a mixture of a powdered form of one or more compounds moistened with one or more inert liquid diluents.

For liquid form preparations, active compounds can be mixed with water or other solvent, solubilizing agents and emulsifiers, for example, ethyl alcohol, isopropanol, ethyl carbonate, ethyl acetate, benzyl alcohol, benzyl benzoate, propylene glycol, 1,3-butylene glycol, dimethylformamide, oils (for example, cottonseed, groundnut, corn, germ, olive, castor and sesame oil), glycerol, fatty acid esters of sorbitan or mixtures thereof.

Aqueous solutions suitable for oral use can be prepared by dissolving the active component in water and adding suitable colorants, flavors, stabilizers, wetting agents, emulsifying agents, suspending agents, sweetening agents, flavoring agents, perfuming agents and thickening agents as desired. Aqueous suspension suitable for oral use can be made by dispersing the finely divided active component in water with viscous material, for example, natural or synthetic gums, resins, methyl cellulose, sodium carboxymethyl cellulose and other suspending agents. Other liquid form preparations include, for example, water or water-propylene glycol solutions for parenteral injection. Other injectable preparations, for example, sterile injections, injectable depot forms, aqueous suspensions may be formulated according to the art using suitable dispersing or wetting and suspending agent. Among the acceptable vehicles and solvents that may be employed are water, Ringer's solution and isotonic sodium chloride.

Such solutions are prepared so as to be acceptable to biological systems with respect to isotonicity, pH, and other parameters. Liquid preparations can also be formulated in solution in aqueous polyethylene glycol solution.

Ointment preparations can contain one or more compounds described herein or salts thereof with a physiologically acceptable carrier. Such salts can be heavy metal salts. The carrier can desirably be a conventional water-dispersible hydrophilic or oil-in-water carrier, particularly a conventional semi-soft or cream-like water-dispersible or water soluble, oil-in-water emulsion infected surface with a minimum of discomfort. Suitable compositions may be prepared by merely incorporating or homogeneously admixing finely divided compounds with the hydrophilic carrier or base or ointment.

Dosage forms for tropical or transdermal administration of one or more compounds described herein includes ointments, pastes, creams, lotions, gels, powders, solutions, sprays, inhalants or patches. Active compounds can be admixed under sterile condition with one or more pharmaceutically acceptable carriers and any desired preservatives or buffers as may be required. Ophthalmic formulations, eardrops, eye ointments, powders and solutions are also encompassed within the scope of this invention.

The pharmaceutical preparation can be in unit dosage form. In such forms, the preparation can be subdivided into unit doses containing appropriate quantities of the active component, i.e., one or more compounds described herein and optionally one or more other therapeutic agents. Dosage forms can be a packaged preparation containing one or more discrete unit dosages, for example, capsules, tablets, powders in vials, capsules or ampoules, ointments, cachets, gels or gel caps, cream itself, dispersible granules, suppositories, troches, patches, magmas, lozenges, pastes, plasters, lotions, discs, ointments, solutions, suspensions, emulsions, syrups, elixirs, aerosols, nasal spays or oral sprays.

The magnitude of a prophylactic or therapeutic dose of one or more compounds described herein in the acute or chronic prevention, treatment, or management of a disorder or condition will vary with the severity of the condition to be treated and the route of administration. The dose, and perhaps the dose frequency, will also vary according to the age, body weight, and response of the individual patient. Suitable total daily dose ranges can be readily determined by those skilled in the art. In general, the total daily dose range for one or more compounds described herein, for the conditions described herein, is from about 1 mg to about several grams administered in single or divided doses according to the particular application and the potency of the active ingredient. Compounds described herein can also be administered at initial dosages of about 3 mg to about 40 mg per kilogram daily. Suitable dosage amounts can be determined using small dosages that are less than the optimum dose. Such small dosages can be increased in small increments until the optimum effect is reached. Dosage amounts may be divided and administered as divided doses if desired.

Any suitable route of administration may be employed for providing the patient with an effective dosage of one or more compounds described herein according to the methods of the present invention. For example, oral, intraoral, rectal, parenteral, epicutaneous, transdermal, subcutaneous, intramuscular, intranasal, sublingual, buccal, intradural, intraocular, intrarespiratory, or nasal inhalation and like forms of administration may be employed. Oral administration is generally preferred.

In addition to the common dosage forms set out above, the compound for use in the methods of the present invention may also be administered by controlled release means and/or delivery devices such as those described in, for example, U.S. Pat. Nos. 3,845,770; 3,916,899; 3,536,809; 3,598,123; and 4,008,719, the pertinent disclosures of which are incorporated herein by reference.

In one aspect, provided are processes for synthesizing compounds of Formula I. Pharmaceutically acceptable nontoxic acid addition salts of the compounds described herein may be formed with inorganic or organic acids, by methods well-known in the art.

The present invention also includes within its scope prodrugs of the compounds of Formula I. In general, such prodrugs will be functional derivatives of these compounds, which readily get converted in vivo into defined compounds. Conventional procedures for the selection and preparation of suitable prodrugs are known to the artisan of ordinary skill in the art.

The invention also includes pharmaceutically acceptable salts, pharmaceutically acceptable solvates, the enantiomers, diastereomers, N-oxides, prodrugs, metabolites in combination with a pharmaceutically acceptable carrier and optionally included excipients.

Other advantages of the invention will be set forth in the description which follows, and in part will be apparent from the description, or may be learned by the practice of the invention.

The following definitions apply to terms as used herein:

The term "alkyl," unless otherwise specified, refers to a monoradical branched or unbranched saturated hydrocarbon chain having from 1 to 20 carbon atoms. Alkyl groups can be optionally interrupted by atom(s) or group(s) independently selected from oxygen, sulfur, a phenylene, sulphinyl, sulphonyl group or —$NR_a$—, wherein $R_a$ can be hydrogen, alkyl, alkenyl, alkynyl cycloalkyl or aryl. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further (referred herein as "substituted alkyl") with one or more substituents selected from alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, aryl, heterocyclyl, heteroaryl, (heterocyclyl)alkyl, cycloalkoxy, —CH=N—O($C_{1-6}$alkyl), —CH=N—NH ($C_{1-6}$ alkyl), —CH=N—NH($C_{1-6}$alkyl)-$C_{1-6}$alkyl, arylthio, thiol, alkylthio, aryloxy, nitro, aminosulfonyl, aminocarbonylamino, —NHC(=O)$R_p$, —$NR_pR_g$, —C(=O)$NR_pR_g$, —NHC(=O)$NR_pR_g$, —C(=O)heteroaryl, C(=O)heterocyclyl, —O—C(=O)$NR_pR_g$ {wherein $R_p$ and $R_g$ are independently selected from hydrogen, alkyl, alkenyl, alkynyl, cycloalkyl, alkoxy, cycloalkenyl, aryl, aralkyl, heterocyclyl, heteroaryl, heterocyclylalkyl, heteroarylalkyl}, nitro, hydroxyamino, alkoxyamino or S(O)$_m$R$_{66}$ (wherein m is an integer from 0-2 and $R_{66}$ is alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, alkenyl, alkynyl, carboxy, —$NR_pR_g$, —C(=O)$NR_pR$, —OC(=O)$NR_pR_g$, —NHC (=O)$NR_pR_g$ (wherein $R_p$ and $R_g$ are the same as defined earlier), hydroxy, alkoxy, halogen, $CF_3$, cyano, and S(O)$_m$R$_{66}$ (wherein m is an integer from 0-2 and $R_{66}$ are the same as defined earlier); or an alkyl group also may be interrupted by 1-5 atoms of groups independently selected from oxygen, sulfur or —$NR_a$— {wherein $R_a$ is selected from hydrogen, alkyl, cycloalkyl, alkenyl, cycloalkenyl, alkynyl, aryl, acyl, aralkyl, —C(=O)$OR_p$ (wherein $R_p$ is the same as defined earlier), S(O)$_m$R$_{66}$ (wherein m is an integer from 0-2 and $R_{66}$ is as defined earlier), or —C(=O)$NR_pR_g$ (wherein $R_p$ and $R_g$ are as defined earlier)}. Unless otherwise constrained by the definition, all substituents may be substituted further by 1-3 substituents selected from alkyl, carboxy, carboxyalkyl, —$NR_pR_g$, —C(=O)$NR_pR_g$, —O—C(=O)$NR_pR_g$ (wherein $R_p$ and $R_g$ are the same as defined earlier) hydroxy, alkoxy, halogen, $CF_3$, cyano, and S(O)$_m$R$_{66}$ (wherein m is an integer from 0-2 and $R_{66}$ is same as defined earlier); or an alkyl group as defined above that has both substituents as defined above and is also interrupted by 1-5 atoms or groups as defined above.

The term "alkenyl," unless otherwise specified, refers to a monoradical of a branched or unbranched unsaturated hydrocarbon group having from 2 to 20 carbon atoms with cis, trans, or geminal geometry. It can be optionally interrupted by atom(s) or group(s) independently chosen from oxygen, sulfur, phenylene, sulphinyl, sulphonyl and —$NR_a$—, wherein $R_a$ can be hydrogen, alkyl, alkenyl, alkynyl, cycloalkyl or aryl. In the event that alkenyl is attached to a heteroatom, the double bond cannot be alpha to the heteroatom. Alkenyl groups may be substituted further (referred to herein as "substituted alkenyl") with one or more substituents selected from alkyl, alkenyl, alkynyl, alkoxy, cycloalkyl, cycloalkenyl, acyl, acylamino, acyloxy, —NHC(=O)$R_p$, —$NR_pR_g$, —C(=O)$NR_pR_g$, —NHC(=O)$NR_pR_g$, —O—C(=O)$NR_pR_g$ (wherein $R_p$ and $R_g$ are the same as defined earlier), alkoxycarbonylamino, azido, cyano, halogen, hydroxy, oxo, keto, carboxyalkyl, thiocarbonyl, carboxy, arylthio, thiol, alkylthio, aryl, aralkyl, aryloxy, heterocyclyl, heteroaryl, heterocyclyl alkyl, heteroaryl alkyl, aminosulfonyl, aminocarbonylamino, alkoxyamino, hydroxyamino, alkoxyamino, nitro, or $SO_2R_{66}$ (wherein $R_{66}$ are is same as defined earlier). Unless otherwise constrained by the definition, alkenyl substituents optionally may be substituted further by 1-3 substituents selected from alkyl, carboxy, hydroxy, alkoxy, halogen, —$CF_3$, cyano, —$NR_pR_g$, —C(=O)$NR_pR_g$, —O—C (=O)$NR_pR_g$ (wherein $R_p$ and $R_g$ are the same as defined earlier) and —$SO_2R_{66}$ (wherein $R_{66}$ is same as defined earlier). Groups, such as ethenyl or vinyl (CH=$CH_2$), 1-propylene or allyl (—$CH_2$CH=$CH_2$), iso-propylene (—C($CH_3$)=$CH_2$), bicyclo[2.2.1]heptene, and the like, exemplify this term.

The term "alkynyl," unless otherwise specified, refers to a monoradical of an unsaturated hydrocarbon, having from 2 to 20 carbon atoms. It can be optionally interrupted by atom(s) or group(s) independently chosen from oxygen, sulfur, phenylene, sulphinyl, sulphonyl and —$NR_a$—, wherein $R_a$ can be hydrogen, alkyl, alkenyl, alkynyl, cycloalkyl or aryl. In the event that alkynyl is attached to a heteroatom, the triple bond cannot be alpha to the heteroatom. Alkynyl groups may be substituted further (referred to herein as "substituted alkynyl") with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, arylthio, thiol, alkylthio, aryl, aralkyl, aryloxy, aminosulfonyl, aminocarbonylamino, hydroxyamino, alkoxyamino, nitro, heterocyclyl, heteroaryl, heterocyclylalkyl, heteroarylalkyl, —NHC(=O)$R_p$, —$NR_pR_g$, —NHC(=O)$NR_pR_g$, —C(=O)$NR_pR_g$, —O—C(=O)$NR_pR_g$ (wherein $R_p$ and $R_g$ are the same as defined earlier), $S(O)_mR_{66}$ (wherein m is an integer from 0-2 and $R_{66}$ is as defined earlier). Unless otherwise constrained by the definition, alkynyl substituents optionally may be substituted further by 1-3 substituents selected from alkyl, carboxy, carboxyalkyl, hydroxy, alkoxy, halogen, $CF_3$, —$NR_pR_g$, —C(=O)$NR_pR_g$, —NHC(=O)$NR_pR_g$, —C(=O)$NR_pR_g$ (wherein $R_p$ and $R_g$ are the same as defined earlier), cyano, or $S(O)_mR_{66}$ (wherein m is an integer from 0-2 and $R_{66}$ is same as defined earlier). Groups such as ethynyl, (—C≡CH), propargyl (or propynyl, —$CH_2$C≡CH), and the like exemplify this term.

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like, or multiple ring structures, including adamantanyl, and bicyclo[2.2.1]heptane, or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —$NR_pR_g$, —NHC(=O)$NR_pR_g$, —NHC(=O)$R_p$, —C(=O)$NR_pR_g$, —O—C(=O)$NR_pR_g$ (wherein $R_p$ and $R_g$ are the same as defined earlier), nitro, heterocyclyl, heteroaryl, heterocyclylalkyl, heteroarylalkyl, or $S(O)_mR_{66}$ (wherein m is an integer from 0-2 and $R_{66}$ is same as defined earlier). Unless otherwise constrained by the definition, cycloalkyl substituents optionally may be substituted further by 1-3 substituents selected from alkyl, carboxy, hydroxy, alkoxy, halogen, $CF_3$, —$NR_pR_g$, —C(=O)$NR_pR_g$, —NHC(=O)$NR_pR_g$, —O—C(=O)$NR_pR_g$ (wherein $R_p$ and $R_g$ are the same as defined earlier), cyano or $S(O)_mR_{66}$ (wherein m is an integer from 0-2 and $R_{66}$ is same as defined earlier).

The term "alkoxy" denotes the group O-alkyl wherein alkyl is the same as defined above.

The term "aryl" herein refers to aromatic system having 6 to 14 carbon atoms, wherein the ring system can be mono-, bi- or tricyclic and are carbocyclic aromatic groups. For example, aryl groups include, but are not limited to, phenyl, biphenyl, anthryl or naphthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, $CF_3$, cyano, nitro, $COOR_s$ (wherein $R_s$ is hydrogen, alkyl, alkenyl, alkynyl, cycloalkyl, aralkyl, heterocyclylalkyl, heteroarylalkyl), NHC(=O)$R_p$, —$NR_pR_g$, —C(=O)$NR_pR_g$, —NHC(=O)$NR_pR_g$, —O—C(=O)$NR_pR_g$, $S(O)_mR_{66}$ (wherein m is an integer from 0-2 and $R_{66}$ is same as defined earlier), carboxy, optionally substituted heterocyclyl, heteroaryl, heterocyclylalkyl, heteroarylalkyl, amino carbonyl amino, mercapto, haloalkyl, optionally substituted aryl, optionally substituted heterocyclylalkyl, thioalkyl, —CONH$R_p$, —OCO$R_p$, —CO$R_p$, —NHSO$_2R_p$, or —SO$_2$NH$R_p$ (wherein $R_p$ and $R_g$ are the same as defined earlier). The aryl group optionally may be fused with a cycloalkyl group, wherein the cycloalkyl group may optionally contain heteroatoms selected from O, N or S. Groups such as phenyl, naphthyl, anthryl, biphenyl, and the like exemplify this term.

The term "aralkyl," unless otherwise specified, refers to alkyl-aryl linked through an alkyl portion (wherein alkyl is as defined above) and the alkyl portion contains 1-6 carbon atoms and aryl is as defined below. Examples of aralkyl groups include benzyl, ethylphenyl, propylphenyl, naphthylmethyl and the like.

The term "heteroaryl," unless otherwise specified, refers to an aromatic ring structure containing 5 or 6 ring atoms, or a bicyclic or tricyclic aromatic group having from 8 to 14 ring atoms, with one or more heteroatom(s) independently selected from N, O or S. Heteroaryl groups can be optionally substituted with 1 to 4 substituent(s) (referred herein as "substituted heteroaryl") selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —$NR_pR_g$, CH=NOH, —$(CH_2)_wC$(=O)$R_t$ {wherein w is an integer from 0-4 and $R_t$ is hydrogen, hydroxy, $OR_p$, $NR_pR_g$, —NHO$R_z$ or —NHOH}, —C(=O)$NR_pR_g$ and —NHC(=O)$NR_pR_g$, $S(O)_mR_{66}$, —O—C(=O)$NR_pR_g$, —O—C(=O)$R_p$, —O—C(=O)O$R_p$ (wherein m, $R_{66}$, $R_p$ and $R_g$ are as defined earlier, and $R_z$ is alkyl, cycloalkyl, aryl, heteroaryl, heterocyclyl, heteroarylalkyl or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzothiazolyl, or benzoxazolyl, benzthiazinyl, benzthiazinonyl, benzoxazinyl, benzoxazinonyl, quinazonyl, carbazolyl phenothiazinyl, phenoxazinyl and the like.

The term "heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, acyl, optionally substituted aryl, alkoxy, alkaryl, cyano, nitro, oxo, carboxy, optionally substituted heterocyclyl, optionally substituted heterocyclylalkyl, optionally substituted heteroaryl, —O—C(=O)$R_p$, —O—C(=O)O$R_p$, —C(=O)$NR_pR_g$, $S(O)_mR_{66}$, —O—C(=O)$NR_pR_g$, —NHC(=O)$NR_pR_g$, —$NR_pR_g$, $NR_pR_g$, mercapto, haloalkyl, thioalkyl, —COO$R_p$, —COONH$R_p$, —CO$R_p$, —NHSO$_2R_p$, SO$_2$NH$R_p$ (wherein m, $R_{66}$, $R_p$ and $R_g$ are as defined earlier) or guanidine. Such ring systems can be mono-, bi- or tricyclic. Carbonyl or sulfonyl group can replace carbon atom(s) of heterocyclyl. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include oxazolidinyl, tetrahydrofuranyl, dihydrofuranyl, benzoxazinyl, benzthiazinyl, imidazolyl, benzimidazolyl, tetrazolyl, carbaxolyl, indolyl, phenoxazinyl, phenothiazinyl, dihydropyridinyl, dihydroisoxazolyl, dihydrobenzofuryl, azabicyclohexyl, thiazolidinyl, dihydroindolyl, pyridinyl, isoindole 1,3-dione, piperidinyl, tetrahydropyranyl, piperazinyl, 3H-imidazo[4,5-b]pyridine, isoquinolinyl, 1H-pyrrolo[2,3-b]pyridine, and the like.

Unless otherwise constrained by the definition, all substituents optionally may be substituted further by 1-3 substituents selected from alkyl, aralkyl, cycloalkyl, aryl, heteroaryl, heterocyclyl, carboxy, carboxyalkyl, hydroxy, alkoxy, halogen, $CF_3$, cyano, —C(=T)$NR_pR_g$, —O(C=O) $NR_pR_g$ (wherein $R_p$, $R_g$ and T are the same as defined earlier) and —OC(=T)$NR_pR_g$, $S(O)_mR_{66}$ (wherein m is an integer from 0-2 and R66 is the same as defined earlier).

"Heteroarylalkyl" refers to alkyl-heteroaryl group linked through alkyl portion, wherein the alkyl and heteroaryl are the same as defined earlier.

"Heterocyclylalkyl" refers to alkyl-heterocyclyl group linked through alkyl portion, wherein the alkyl and heterocyclyl are the same as defined earlier.

"Acyl" refers to —C(=O)R" wherein R" is selected from the group hydrogen, alkyl, cycloalkyl, aryl, aralkyl, heteroaryl, heterocyclyl, heteroarylalkyl or heterocyclylalkyl.

The term "leaving group" generally refers to groups that exhibit the desirable properties of being labile under the defined synthetic conditions and also, of being easily separated from synthetic products under defined conditions. Examples of such leaving groups includes but not limited to halogen (F, Cl, Br, I), triflates, tosylate, mesylates, alkoxy, thioalkoxy, hydroxy radicals and the like.

The term "protecting groups" refers to moieties that prevent chemical reaction at a location of a molecule intended to be left unaffected during chemical modification of such molecule. Unless otherwise specified, protecting groups may be used on groups, such as hydroxy, amino, or carboxy. Examples of protecting groups are found in T. W. Greene and P. G. M. Wuts, "Protective Groups in Organic Synthesis", $2^{nd}$ Ed., John Wiley and Sons, New York, N.Y., which is incorporated herein by reference. The species of the carboxylic protecting groups, amino protecting groups or hydroxy protecting groups employed are not critical, as long as the derivatized moieties/moiety is/are stable to conditions of subsequent reactions and can be removed without disrupting the remainder of the molecule.

The term "pharmaceutically acceptable salts" refers to derivatives of compounds that can be modified by forming their corresponding acid or base salts. Examples of pharmaceutically acceptable salts include, but are not limited to, mineral or organic acids salts of basic residues (such as amines), or alkali or organic salts of acidic residues (such as carboxylic acids), and the like.

The compounds disclosed herein may be prepared by techniques well-known in the art. In addition, the compounds described herein may be prepared by the following reaction sequences as depicted in schemes I and II below. (The intermediates were prepared following processes described in the references *Eur. J. Pharm. Sci.*, 15, 2002, 367-378; *J. Med. Chem.* 2000, 43, 953-970; *Ind. J. Chem.* 1983, 22(B), 117-120; *J. Med. Chem.* 2003, 46, 2227-2240; *J. Het. Chem.*, 2000, 37, 119-126; *Synth. Comm.* 2003, 33, 3285-3289; *J. Med. Chem.* 2003, 46, 284-302).

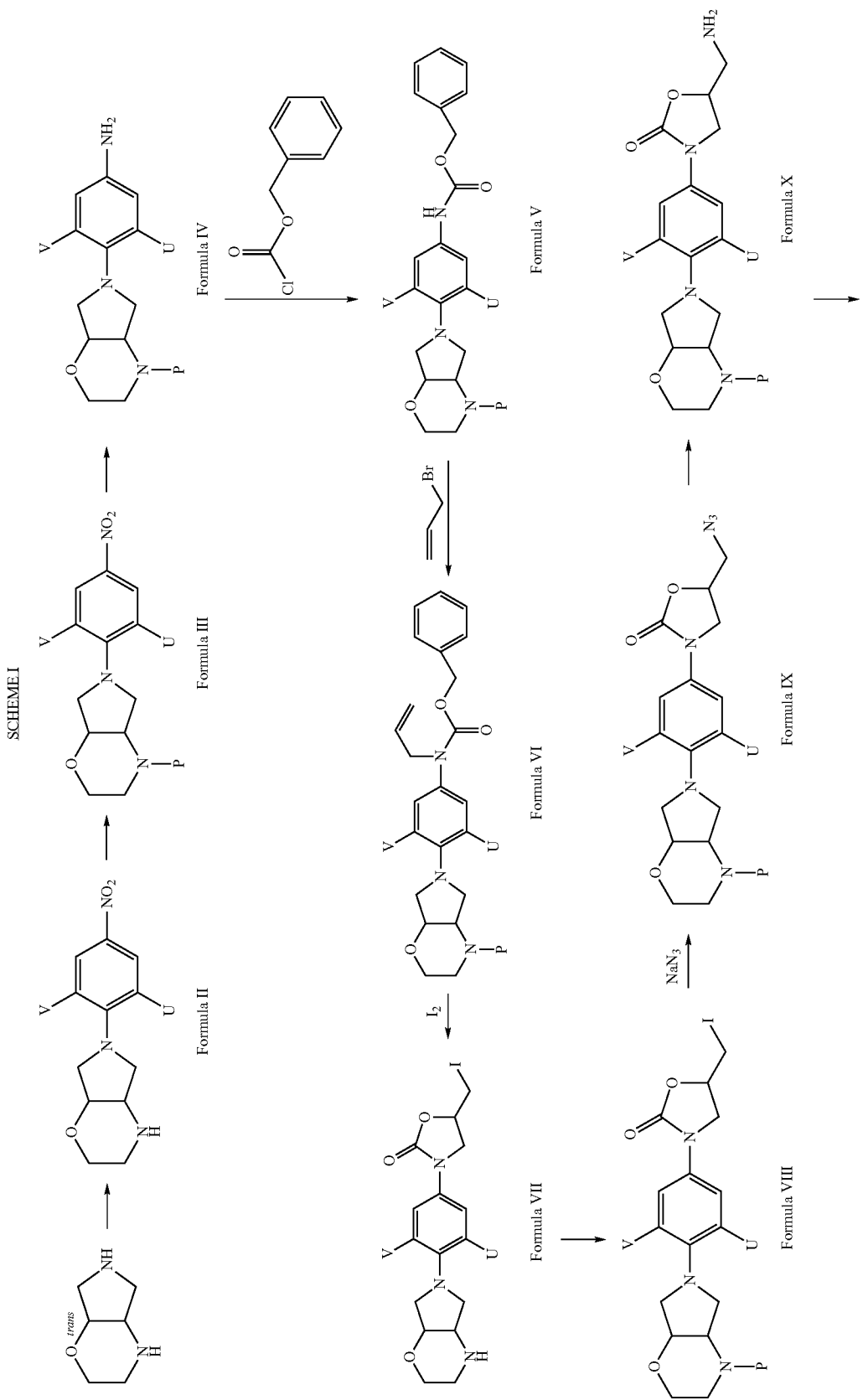

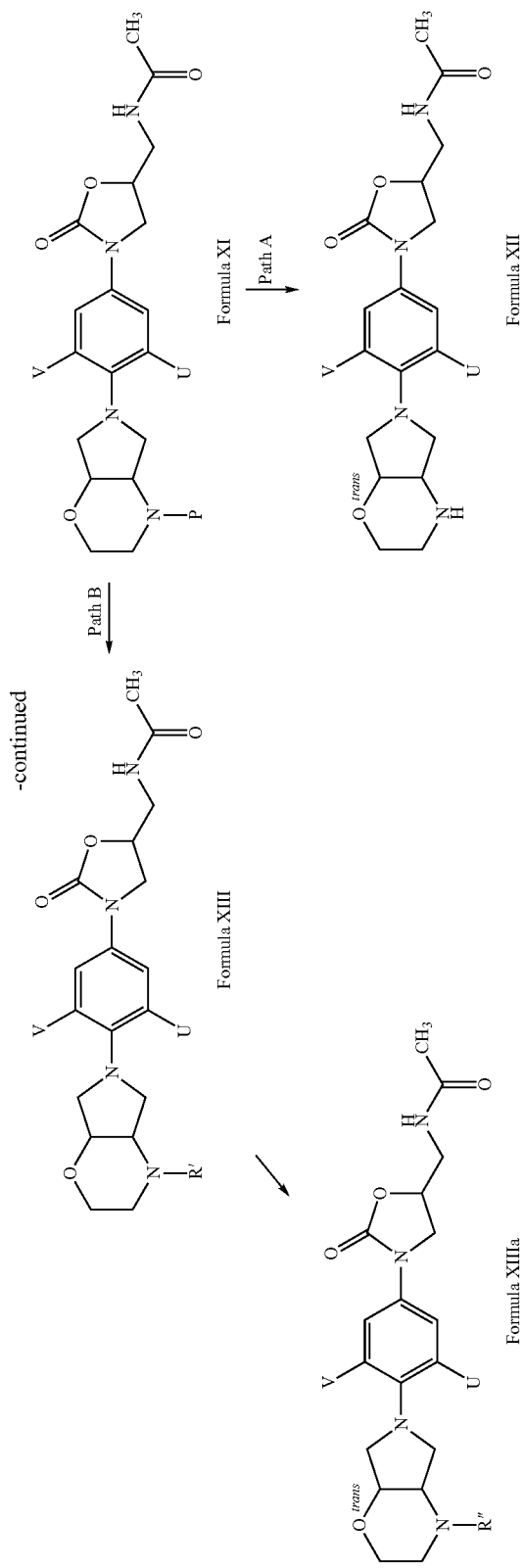

Compounds of Formula VII, VIII, X, XI, XII, XIII and XIIIa can be prepared, for example, by following Scheme I. Thus the compound (7aE)-octahydropyrrolo[3,4-b][1,4]oxazine can be coupled with substituted nitrobenzene to form the compounds of Formula II (wherein U and V are as defined earlier) which can be protected to form compounds of Formula III (wherein P is amine protecting group as tertbutyloxy carbonyl anhydride (BOC) or 9-fluorenylmethyl carbamate (Fmoc)) which in turn can be reduced to form compounds of Formula IV. Compounds of Formula IV can be coupled with [2-(chlorooxy)-2-oxoethyl]benzene to give compounds of Formula V and then can be reacted with 3-bromoprop-1-ene to form compounds of Formula VI. Compounds of Formula VI can be cyclized to give compounds of Formula VII, and then can be protected to form compounds of Formula VIII. Compound of Formula VIII can be azidated to gives compounds of Formula IX and can be further hydrogenated to give the amine of Formula X. Compounds of Formula X can be reacted with acylating agent to form compounds of Formula XI that can be further hydrolysed (Path A) to form compounds of Formula XII. Alternatively Compounds of Formula XI can be reacted with acylating or sulphonating agent (Path B) to form compounds of Formula XIII (wherein R' can be acyl, acetoxyl or sulphonyl). When R' is acetoxyl group then the compounds of Formula XIII can be further deprotected to give compounds of Formula XIIIa (wherein R" is —COCH$_2$OH). (7aE)-octahydropyrrolo[3,4-b][1,4]oxazine can be reacted with substituted nitrobenzene to give the compounds of Formula II in the presence of a base for example diethylisopropylamine, triethylamine or N-methylmorpholine in a solvent for example acetonitrile, dioxane or tetrahydrofuran.

Compounds of Formula II can be protected to give compounds of Formula III in presence of base, for example, sodium hydroxide or potassium hydroxide with protecting agent, for example, tertbutyloxy carbonyl anhydride (BOC) or 9-fluorenylmethyl carbamate (Fmoc) in a solvent, for example, tetrahydrofuran, dimethylformamide, dioxolane, water or mixture thereof.

Compounds of Formula III can be reduced to give a compounds of Formula IV in presence of suitable reducing agent, for example, palladium over carbon or raney nickel. in a solvent, for example, methanol, ethanol or propanol.

Compounds of Formula IV can be reacted with benzyloxy carbonyl chloride to give the compound of Formula V in the presence of base, for example, sodium hydrogen carbonate or potassium hydrogen carbonate in a solvent, for example, tetrahydrofuran, dioxane or dimethyl formamide.

Compounds of Formula V can be reacted with allyl bromide to give a compounds of Formula VI in the presence of a phase transfer catalyst, for example, tetrabutyl ammonium iodide or tetrabutyl ammonium chloride in a solvent, for example, tetrahydrofuran, dioxane or dimethyl formamide and a base, for example, sodium hydride or potassium hydride.

Compounds of Formula VI can be cyclized to give the compounds of Formula VII in the presence of iodine in a solvent, for example, dichloromethane, chloroform or carbon tetrachloride.

Compounds of Formula VII can be protected to give compounds of Formula VIII in the presence of a catalyst, for example, dimethylaminopyridine, 2,6 dimethylpyridine or pyrrolidinopyridine along with protecting agent, for example, tertbutyloxy anhydride (BOC) or 9-fluoroenylmethyl carbamate (Fmoc) in solvent, for example, tetrahydrofuran, dichloromethane, dimethylformamide, dioxolane, water or mixture thereof and a base, for example, triethylamine, diisopropylamine or N-methyl morpholine.

Compounds of Formula VIII can be reacted to give a compounds of Formula IX in the presence of sodium azide or potassium azide in a solvent, for example, dimethyl formamide, dioxane or tetrahydrofuran.

Compounds of Formula IX can be reduced to give the compounds of Formula X in presence of a catalyst, for example, triphenylphosphine or diphenylphosphine in a solvent for example, tetrahydrofuran, dioxane or dimethyl formamide.

Compounds of Formula X can be reacted to give a compounds of Formula XI in the presence of base, for example, trietlylamine, diisopropylamine or N-methyl morpholine with acylating agent, for example, acetic anhydride or acetic acid in a solvent, for example, dichloromethane, chloroform or carbon tetrachloride.

Path A: Compounds of Formula XI can be hydrolysed to give a compounds of Formula XII in the presence of ethanolic or methanolic hydrochloride acid.

Path B: Compounds of Formula XI can be reacted to give the compound of Formula XIII in the presence of a catalyst, for example, dimethylaminopyridine, 2,6 dimethylpyridine or pyrrolidinopyridine with acylating agent or sulphonating agents, for example, acetoxy acetyl chloride, acetyl chloride, benzoyl chloride, or suphonyl chloride in solvent, for example, dimethyl formamide, dimethyl sulphoxide, tetrahydrofuran dioxane or mixture thereof and a base, for example, triethylamine, diisopropylamine or N-methyl morpholine.

Compounds of Formula XIII can be deprotected to give compounds of Formula XIIIa in the presence of a base, for example, potassium carbonate or sodium carbonate, in a solvent, for example methanol, ethanol or propanol Particular illustrative compounds that can be prepared following Scheme I include, for example:

3-{3-fluoro-4-[(7aE)-hexahydropyrrolo[3,4-b][1,4]oxazin-4(4aH)-yl]phenyl}-5-(iodomethyl)-1,3-oxazolidin-2-one (Compound No. 01);

tert-butyl (7aE)-6-{2-fluoro-4-[5-(iodomethyl)-2-oxo-1,3-oxazolidin-3-yl]phenyl}hexahydropyrrolo[3,4-b][1,4]oxazine-4(4aH)-carboxylate (Compound No. 02);

tert-butyl (7aE)-6-{4-[5-(aminomethyl)-2-oxo-1,3-oxazolidin-3-yl]-2-fluorophenyl}hexahydropyrrolo[3,4-b][1,4]oxazine-4(4aH)-carboxylate (Compound No. 03);

tert-butyl (7aE)-6-(4-{5-[(acetylamino)methyl]-2-oxo-1,3-oxazolidin-3-yl}-2-fluorophenyl)hexahydropyrrolo[3,4-b][1,4]oxazine-4(4aH)-carboxylate (Compound No. 04);

N-[(3-{3-fluoro-4-[(7aE)-hexahydropyrrolo[3,4-b][1,4]oxazin-6(2H)-yl]phenyl}-2-oxo-1,3-oxazolidin-5-yl)methyl]acetamide (Compound No. 05);

2-[(7aE)-6-(4-{5-[(acetylamino)methyl]-2-oxo-1,3-oxazolidin-3-yl}-2-fluorophenyl)hexahydropyrrolo[3,4-b][1,4]oxazin-4(4aH)-yl]-2-oxoethyl acetate (Compound No. 06);

N-[(3-{4-[(7aE)-4-acetylhexahydropyrrolo[3,4-b][1,4]oxazin-6(2H)-yl]-3-fluorophenyl}-2-oxo-1,3-oxazolidin-5-yl)methyl]acetamide (Compound No. 07);

N-[(3-{4-[(7aE)-4-benzoylhexahydropyrrolo[3,4-b][1,4]oxazin-6(2H)-yl]-3-fluorophenyl}-2-oxo-1,3-oxazolidin-5-yl)methyl]acetamide (Compound No. 08);

N-[(3-{3-fluoro-4-[(7aE)-4-(4-fluorobenzoyl)hexahydropyrrolo[3,4-b][1,4]oxazin-6(2H)-yl]phenyl}-2-oxo-1,3-oxazolidin-5-yl)methyl]acetamide (Compound No. 09);

N-[(3-{3-fluoro-4-[(7aE)-4-(methylsulfonyl)hexahydropyrrolo[3,4-b][1,4]oxazin-6(2H)-yl]phenyl}-2-oxo-1,3-oxazolidin-5-yl)methyl]acetamide (Compound No. 10);

N-[(3-{3-fluoro-4-[(7aE)-4-glycoloylhexahydropyrrolo[3,4-b][1,4]oxazin-6(2H)-yl]phenyl}-2-oxo-1,3-oxazolidin-5-yl)methyl]acetamide (Compound No. 11).

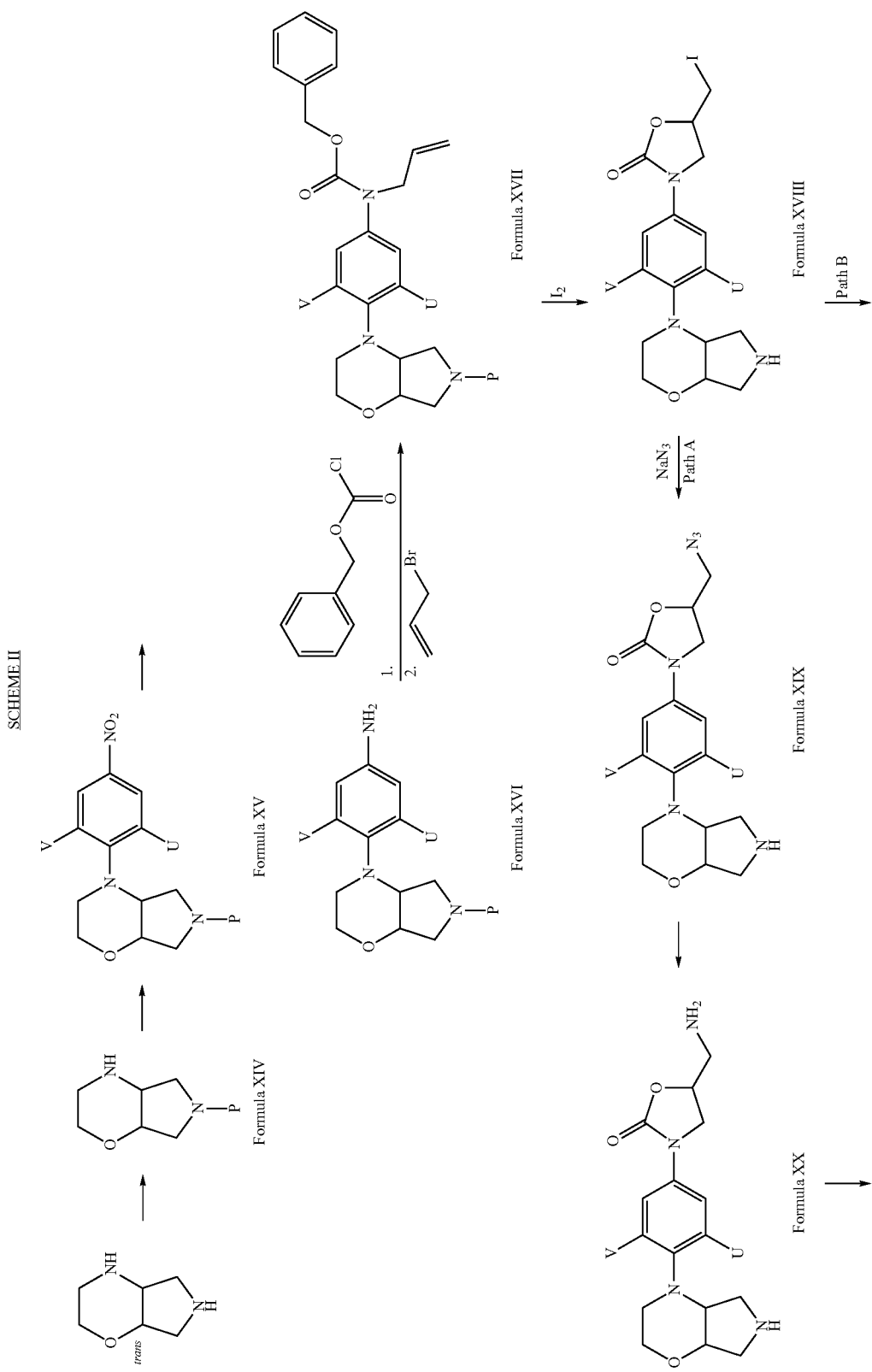

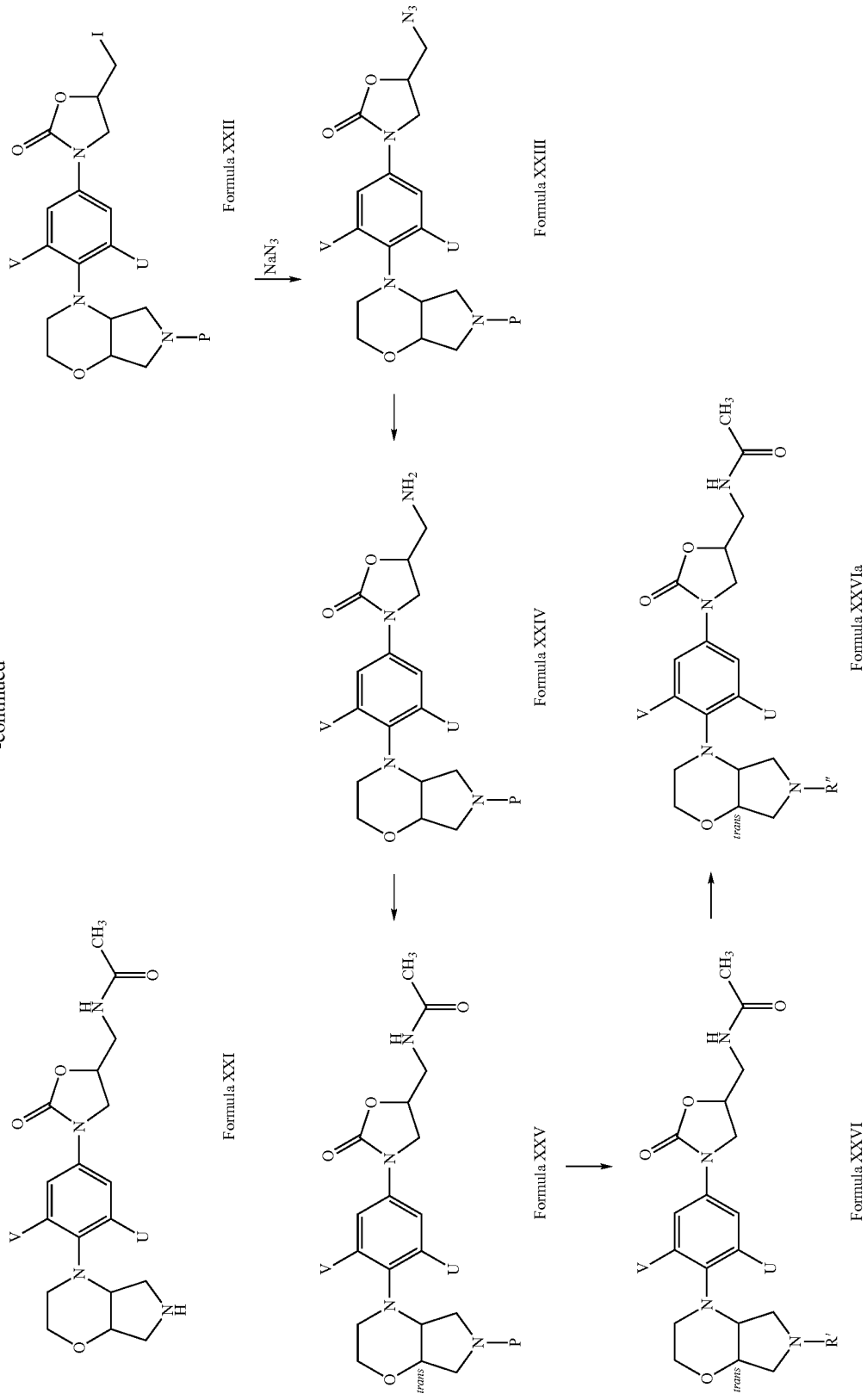

Compounds of Formula XVIII, XXI, XXII, XXV, XXVI and XXVIa can be prepared, for example, by following Scheme II. Thus, the compound (7aE)-octahydropyrrolo[3,4-b][1,4]oxazine can be protected to form compounds of Formula XIV, which can be coupled with substituted nitrobenzene to form compounds of Formula XV, which can be further reduced to form compounds of Formula XVI. Compounds of Formula XVI can be reacted with [2-(chlorooxy)-2-oxoethyl] benzene and further with 3-bromoprop-1-ene to form compounds of Formula XVII and can be cyclized in the presence of iodine to form compounds of Formula XVIII. Compounds of Formula XVIII can undergoes azidation to form compounds of Formula XIX (path A) and can be reduced to form compounds of Formula XX which can be further acylated to form compounds of Formula XXI. Compounds of Formula XVIII can be protected to form compounds of Formula XXII (path B) which can be azidated to form compounds of Formula XXIII. Compounds of Formula XXIII can be reduced and acylated to form compounds of Formula XXIV and XXV, respectively. Compounds of Formula XXV can be deprotected followed by acylation or sulphonation to form compounds of Formula XXVI (where R' can be acyl, acetoxyl or sulphonyl). When R' is acetoxyl group then the compounds of Formula XXVI can be further deprotected to form compounds of Formula XXVIa (wherein R" is —COCH$_2$OH).

(7aE)-octahydropyrrolo[3,4-b][1,4]oxazine can be protected to form compounds of Formula XIV in presence of base, for example, sodium hydroxide or potassium hydroxide with protecting agent, for example, tertbutyloxy carbonyl anhydride (BOC) or 9-fluorenylmethyl carbamate (Fmoc) in a solvent, for example, tetrahydrofuran, dimethylformamide, dioxolane, water or mixture thereof.

Compounds of Formula XIV can be reacted with substituted nitrobenzene to form compounds of Formula XV in the presence of a base, for example, potassium carbonate or sodium carbonate, in a solvent, for example, dimethylformamide, tetrahydrofuran or dioxane.

Compounds of Formula XV can be reduced to form compounds of Formula XVI with suitable reducing agent, for example, palladium over carbon or Raney nickel, in a solvent, for example, ethanol, methanol or propanol.

Compounds of Formula XVI can be reacted with benzyloxy carbonyl chloride to give compounds of Formula XVII in the presence of base, for example sodium hydrogen carbonate or potassium hydrogen carbonate, in solvents, for example tetrahydrofuran, dioxane or dimethyl formamide and further can be reacted with allyl bromide in base, for example, sodium hydride or potassium hydride in the presence of a phase transfer catalyst, for example tetrabutyl ammonium iodide or tetrabutyl ammonium chloride, in a solvent, for example, tetrahydrofuran, dioxane or dimethyl formamide.

The cyclisation of the Compounds of Formula XVII can be cyclized to form compounds of Formula XVIII can be carried out in the presence of iodine in a solvent, for example, dichloromethane, chloroform or carbon tetrachloride.

Path A. Compounds of Formula XVIII can be reacted to form compounds of Formula XIX in the presence of sodium azide or potassium azide, in solvents for example, dimethyl formamide, dioxane or tetrahydrofuran.

Compounds of Formula XIX can be reduced to form compounds of Formula XX in presence of a triphenylphosphine or diphenylphosphine, in a solvent, for example, tetrahydrofuran, dioxane or dimethyl formamide.

Compounds of Formula XX can be reacted to give the compound of Formula XXI in presence of catalyst for example dimethylaminopyridine, 2,6 dimethylpyridine or pyrrolidinopyridine with acylating agent, for example, acetic anhydride or acetic acid in a solvent, for example, dimethyl formamide, dimethyl sulphoxide, tetrahydrofuran or dioxane and a base, for example, diisopropylamine, triethylamine or N-methyl morpholine.

Path B: Compounds of Formula XVIII can be protected to give a compounds of Formula XXII in presence of a catalyst for example dimethylaminopyridine, 2,6 dimethylpyridine or pyrrolidinopyridine with protecting agent, for example, tert-butyloxy carbonyl anhydride (BOC) or 9-fluorenylmethyl carbamate (Fmoc) in a solvent, for example, tetrahydrofuran, dichloromethane, dimethylformamide, dioxolane, water or mixture thereof and a base, for example, triethylamine, diisopropylamine or N-methyl morpholine.

Compounds of Formula XXII can be reacted to give a compounds of Formula XXIII in the presence of sodium azide or potassium azide in a solvent, for example, dimethyl formamide, dioxane or tetrahydrofuran.

Compounds of Formula XIII can be reduced to give the compounds of Formula XXIV in presence of a catalyst, for example, triphenylphosphine or diphenylphosphine in a solvent, for example, tetrahydrofuran, dioxane or dimethyl formamide.

Compounds of Formula XXIV can be reacted to give the compounds of Formula XXV in the presence of base, for example, triethylamine, diisopropylamine or N-methyl morpholine with acylating agent, for example, acetic anhydride or acetic acid in a solvent, for example, dichloromethane, carbon tetrachloride or chloroform.

Compounds of Formula XXV can be deprocted in ethanloic hydrochloride and further acylated or sulphonated with acylating agent or sulphonating agents to form compounds of Formula XXVI in presence of a catalyst, for example, dimethylaminopyridine, 2,6 dimethylpyridine or pyrrolidinopyridine in a solvent for example dimethyl formamide, dimethyl sulphoxide, tetrahydrofuran or dioxane and a base, for example, diisopropylamine, triethylamine or N-methyl morpholine.

Compounds of Formula XXVI can be deprotected to form compounds of Formula XXVIa in the presence of a base, for example, potassium carbonate or sodium carbonate in a solvent, for example, methanol, ethanol or propanol.

Particular illustrative compounds that can be prepared following Scheme II include, for example:

3-{3-fluoro-4-[(7aE)-hexahydropyrrolo[3,4-b][1,4]oxazin-4 (4aH)-yl]phenyl}-5-(iodomethyl)-1,3-oxazolidin-2-one (Compound No. 12);

N-[(3-{3-fluoro-4-[(7aE)-hexahydropyrrolo[3,4-b][1,4]oxazin-4(4aH)-yl]phenyl}-2-oxo-1,3-oxazolidin-5-yl)methyl]acetamide (Compound No. 13);

tert-butyl (7aE)-4-{2-fluoro-4-[5-(iodomethyl)-2-oxo-1,3-oxazolidin-3-yl]phenyl}hexahydropyrrolo[3,4-b][1,4]oxazine-6(2H)-carboxylate (Compound No. 14);

tert-butyl (7aE)-4-(4-{5-[(acetylamino)methyl]-2-oxo-1,3-oxazolidin-3-yl}-2-fluorophenyl)hexahydropyrrolo[3,4-b][1,4]oxazine-6(2H)-carboxylate (Compound No. 15);

2-[(7aE)-4-(4-{5-[(acetylamino)methyl]-2-oxo-1,3-oxazolidin-3-yl}-2-fluorophenyl)hexahydropyrrolo[3,4-b][1,4]oxazin-6(2H)-yl]-2-oxoethyl acetate (Compound No. 16);

N-[(3-{4-[(7aE)-6-benzoylhexahydropyrrolo[3,4-b][1,4]oxazin-4(4aH)-yl]-3-fluorophenyl}-2-oxo-1,3-oxazolidin-5-yl)methyl]acetamide (Compound No. 17);

N-[(3-{4-[(7aE)-6-acetylhexahydropyrrolo[3,4-b][1,4]oxazin-4(4aH)-yl]-3-fluorophenyl}-2-oxo-1,3-oxazolidin-5-yl)methyl]acetamide (Compound No. 18);

N-[(3-{3-fluoro-4-[(7aE)-6-(methylsulfonyl)hexahydropyrrolo[3,4-b][1,4]oxazin-4(4aH)-yl]phenyl}-2-oxo-1,3-oxazolidin-5-yl)methyl]acetamide (Compound No. 19); and N-[(3-{3-fluoro-4-[(7aE)-6-glycoloylhexahydropyrrolo[3,4-b][1,4]oxazin-4(4aH)-yl]phenyl}-2-oxo-1,3-oxazolidin-5-yl)methyl]acetamide (Compound No. 20).

TABLE

Formula I wherein U is hydrogen and V is fluorine;

| Compound No. | A | R | R₁ |
|---|---|---|---|
| 01 | Formula A (trans) | H | —I |
| 02 | Formula A (trans) | —C(O)OC(CH₃)₃ | —I |
| 03 | Formula A (trans) | —C(O)OC(CH₃)₃ | —NH₂ |
| 04 | Formula A (trans) | —C(O)OC(CH₃)₃ | —NHCOCH₃ |
| 05 | Formula A (trans) | H | —NHCOCH₃ |
| 07 | Formula A (trans) | —C(O)CH₃ | —NHCOCH₃ |
| 08 | Formula A (trans) | —C(O)C₆H₅ (phenyl ketone) | —NHCOCH₃ |

TABLE-continued

Formula I wherein U is hydrogen and V is fluorine;

| Compound No. | A | R | R₁ |
|---|---|---|---|
| 09 | Formula A (N-methyl, trans) | —C(O)—C₆H₄—F (4-fluorobenzoyl) | —NHCOCH₃ |
| 06 | Formula A (N-methyl, trans) | —COCH₂OCOCH₃ | —NHCOCH₃ |
| 11 | Formula A (N-methyl, trans) | —COCH₂OH | —NHCOCH₃ |
| 10 | Formula A (N-methyl, trans) | —S(O)₂CH₃ | —NHCOCH₃ |
| 12 | Formula B (trans) | H | I |
| 13 | Formula B (trans) | H | —NHCOCH₃ |
| 14 | Formula B (trans) | —C(O)OC(CH₃)₃ | I |

TABLE-continued
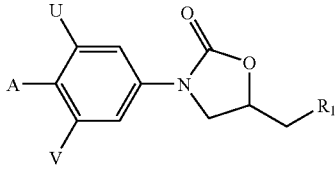
Formula I
wherein U is hydrogen and V is fluorine;
| Compound No. | A | R | $R_1$ |
|---|---|---|---|
| 15 | Formula B 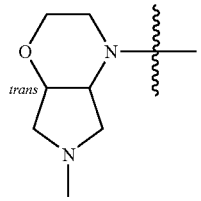 trans | —C(O)OC(CH$_3$)$_3$ | —NHCOCH$_3$ |
| 16 | Formula B 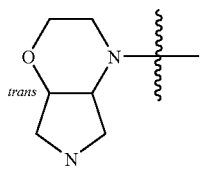 trans | —COCH$_2$OCOCH$_3$ | —NHCOCH$_3$ |
| 17 | Formula B 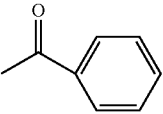 trans | | —NHCOCH$_3$ |
| 18 | Formula B 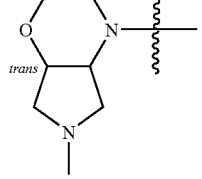 trans | —C(O)CH$_3$ | —NHCOCH$_3$ |
| 19 | Formula B 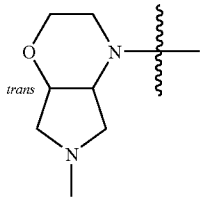 trans | —S(O)$_2$CH$_3$ | —NHCOCH$_{3s}$ |

TABLE-continued

Formula I wherein U is hydrogen and V is fluorine;

| Compound No. | A | R | $R_1$ |
|---|---|---|---|
| 20 | 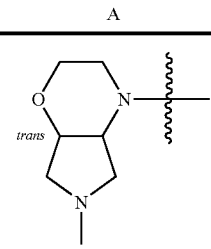 trans | —COCH$_2$OH | —NHCOCH$_3$ |

Formula B

While the present invention has been described in terms of its specific embodiments, certain modifications and equivalents will be apparent to those skilled in the art and are included within the scope of the present invention. The examples are provided to illustrate particular aspects of the disclosure and do not limit the scope of the present invention as defined by the claims.

EXAMPLES

Example 1

Synthesis of 3-[3-fluoro-4-(hexahydropyrrolo[3,4-b][1,4]oxazin-6(2H)-yl)phenyl]-5-(iodomethyl)-1,3-oxazolidin-2-one (Compound No. 01)

Step a: Synthesis 6-(2-fluoro-4-nitrophenyl)octahydropyrrolo[3,4-b][1,4]oxazine

A solution of diethyl isopropyl amine (19.59 mL) and 3,4-dinitrobenzene (10.2 mL) were added to a compound (7aE)-octahydropyrrolo[3,4-b][1,4]oxazine (12 g) (prepared as per the procedure given in DE4200415) in acetonitrile (200 mL) and the reaction mixture was refluxed for about 10 hrs at 80° C. The reaction mixture was concentrated and the crude product was taken in water and extracted with ethyl acetate. The organic layer was washed with water and brine and dried over sodium sulphate. The compound thus obtained was triturated with hexane and the organic layer was evaporated to furnish the title compound (22.1 g).

Step b: Synthesis tert-butyl 6-(2-fluoro-4-nitrophenyl)hexahydropyrrolo[3,4-b][1,4]oxazine-4(4aH)-carboxylate A solution of 10% sodium hydroxide (89.1 mL) was added a to the compound (22.1 g) obtained from the step a above in a mixture of tetrahydrofuran and water (130 mL:65 mL) w followed by the addition of tertbutyloxy carbonyl anhydride (24.6 mL) and stirring for about 24 hrs at room temperature. The reaction mixture was distilled, acidified with citric acid and extracted with ethyl acetate. The organic layer was washed with water and brine and dried over sodium sulphate. The compound thus obtained was triturated with hexane and the organic layer was evaporated to furnish the title compound (27 g).

Step c: Synthesis tert-butyl 6-(4-amino-2-fluorophenyl)hexahydropyrrolo[3,4-b][1,4]oxazine-4(4aH)-carboxylate 5% Pd/C (4 g) was added to the compound (27 g) obtained from the step b above in methanol and hydrogenated at 50 psi for about 3 to 4 hrs. The reaction mixture was filtered through a celite bed and the organic layer was concentrated to yield the title compound (23.7 g)

Step d: Synthesis tert-butyl 6-(4-{[(benzyloxy)carbonyl]amino}-2-fluorophenyl)hexahydropyrrolo[3,4-b][1,4]oxazine-4(4aH)-carboxylate Sodium hydrogen carbonate (9.07 g) and benzyloxy chloride (15.4 mL) were added to the compound (9.1 g) obtained from the step c above in tetrahydrofuran (250 mL) at 0° C. and the reaction mixture was stirred for about 3 hrs. The reaction mixture was filtered and the organic layer was concentrated to get the title compound (16.8 g)

Step e: Synthesis tert-butyl 6-(4-{allyl[(benzyloxy)carbonyl]amino}-2-fluorophenyl)hexahydropyrrolo[3,4-b][1,4]oxazine-4(4aH)-carboxylate Sodium hydride (2.43 g) was added to the solution of the compound (31.8 g) obtained from the step d above in tetrahydrofuran (200 mL) cooled to 0° C., the reaction mixture was stirred for half an hour, followed by the addition of allyl bromide (8.22 mL) and tetrabutyl ammonium iodide (3.18 g) and further stirred for about 1 hour at room temperature. The reaction mixture was quenched with ice water and the compound was extracted with ethyl acetate. The organic layer was washed with water and brine, dried over anhydrous sodium sulphate and concentrated to yield the title compound (33.8 g)

Step f: Synthesis 3-[3-fluoro-4-(hexahydropyrrolo[3,4-b][1,4]oxazin-6(2H)-yl)phenyl]-5-(iodomethyl)-1,3-oxazolidin-2-one (Compound No. 01)

Iodine (46.99 g) was added to the compound (33.8 g) obtained from the step e above in dichloromethane (300 mL) and the reaction mixture was stirred for 17 hrs at room temperature. The reaction mixture was washed with sodium thiosulphate. The organic layer thus separated was washed with water and dried over anhydrous sodium sulphate and concentrated to yield the title compound. (19.4 g)
$^1$H NMR (CDCl$_3$) δ: 9.5 (bs, 1H), 7.46-7.41 (dd, 1H), 7.1-7.07 (d, 1H), 6.69 (t, 1H), 4.71 (m, 1H), 4.42 (m, 1H), 4.16 (t, 1H), 3.98 (m, 2H), 3.75-3.52 (m, 10H)
m/z: M+1=448.31

Example 2

Synthesis of tert-butyl 6-{2-fluoro-4-[5-(iodomethyl)-2-oxo-1,3-oxazolidin-3-yl]phenyl}hexahydropyrrolo[3,4-b][1,4]oxazine-4(4aH)-carboxylate (Compound No. 02)

Triethyl amine (8.72 mL), tertbutyloxy carbonyl anhydride (12.47 mL) and dimethylamino pyridine (5.09 g) was added to the solution of the compound obtained from step f of example 01 in a mixture of dichloromethane and tetrahydrofuran (400:50 mL) and stirred for about 2 hrs at 0° C. and further overnight at room temperature. The reaction mixture was extracted with dichloromethane and the organic layer was washed with sodium hydrogen carbonate, citric acid and water dried over anhydrous sodium sulphate and concentrated to yield the title compound (14.8 g).
$^1$H NMR (CDCl$_3$) δ: 7.36-7.31 (dd, 1H), 7.07-7.04 (d, 1H), 6.62 (t, 1H), 4.71-4.70 (m, 1H), 4.11-3.21 (m, 14H), 1.49 (s, 9H)
m/z: M+1=548.29; M+23=570.35

Example 3

Synthesis of tert-butyl 6-{4-[5-(aminomethyl)-2-oxo-1,3-oxazolidin-3-yl]-2-fluorophenyl}hexahydropyrrolo[3,4-b][1,4]oxazine-4(4aH)-carboxylate (Compound No. 03)

Step a: Synthesis tert-butyl 6-{4-[5-(azidomethyl)-2-oxo-1,3-oxazolidin-3-yl]-2-fluorophenyl}hexahydropyrrolo[3,4-b][1,4]oxazine-4(4aH)-carboxylate Sodium azide (1.21 g) was added to the compound tertbutyl 6-{2-fluoro-4-[5-(iodomethyl)-2-oxo-1,3-oxazolidin-3-yl]phenyl}hexahydropyrrolo[3,4-b][1,4]oxazine-4(4aH)-carboxylate (2 g) obtained from example 02 above in dimethyl formamide (30 mL) and the reaction mixture was stirred at 60° C. for 3 hrs. The reaction mixture was filtered and the filtrate was concentrated to give the title compound (2.1 g).

Step b: Synthesis tert-butyl 6-{4-[5-(aminomethyl)-2-oxo-1,3-oxazolidin-3-yl]-2-fluorophenyl}hexahydropyrrolo[3,4-b][1,4]oxazine-4(4aH)-carboxylate. (Compound No. 03)

Triphenyl phosphine was added to the compound obtained from the step a above in dry tetrahydrofuran and the reaction mixture was stirred for about 2 hrs. To the reaction mixture was added water and was further refluxed for 5 hrs at 40° C. The reaction mixture was concentrated and acidified with 1N hydrochloric acid and extracted with ethyl acetate and water. The aqueous layer was basified with 1 N sodium hydroxide and extracted with ethyl acetate and water. The organic layer was dried over anhydrous sodium sulphate and concentrated to give the title compound (7.3 g).
$^1$H NMR (CDCl$_3$) δ: 7.68-6.67 (m, 1H), 7.46 (m, 2H), 7.07-7.04 (d, 1H), 6.59 (t, 1H), 4.63 (m, 1H), 4.04-2.95 (m, 14H), 1.49 (s, 9H)
m/z: M-Boc.=337.40; M+1=437.44

Example 4

Synthesis of tert-butyl 6-(4-{5-[(acetylamino)methyl]-2-oxo-1,3-oxazolidin-3-yl}-2-fluorophenyl)hexahydropyrrolo[3,4-b][1,4]oxazine-4(4aH)-carboxylate (Compound No. 04)

Triethyl amine (2.77 mL) was added to the compound (5.8 g) obtained form the step b of Example 03 above, in dichloromethane (200 mL) at 0° C., and stirred for about 10 minutes followed by the addition of acetic anhydride (1.52 mL) and father stirred for 2 hrs. The reaction mixture was poured in water and extracted with dichloromethane. The organic layer was washed with sodium hydrogen carbonate followed by brine and dried over anhydrous sodium sulphate and concentrated and purified by column using 2% methanol in dichloromethane as eluant to give the title compound (5 g).
$^1$H NMR (CDCl$_3$) δ: 7.02-6.99 (d, 1H), 6.58 (t, 1H), 6.07 (m, 1H), 4.74 (m, 1H), 4.03-3.39 (m, 15H), 2.02 (s, 3H), 1.49 (s, 9H)
m/z: M+1=479.50; M+23=501.47

Example 5

Synthesis of N-({3-[3-fluoro-4-(hexahydropyrrolo[3,4-b][1,4]oxazin-6(2H)-yl)phenyl]-2-oxo-1,3-oxazolidin-5-yl}methyl)acetamide (Compound No. 05)

Ethanolic hydrochloride was added to the compound (400 mg) obtained from Example 04 above, and stirred for about 2 hrs. The reaction mixture was concentrated and dried to obtain the title compound (440 mg).
$^1$H NMR (DMSO) δ: 10.08 (bs, 1H), 9.63 (bs, 1H), 8.30-8.26 (dd, 1H), 7.12 (d, 1H), 6.74 (t, 1H), 4.69 (m, 1H), 4.36-3.08 (m, 14H), 1.84 (s, 3H)
m/z: M+1=379.39

Example 6

Synthesis of 2-[6-(4-{5-[(acetylamino)methyl]-2-oxo-1,3-oxazolidin-3-yl}-2-fluorophenyl)hexahydropyrrolo[3,4-b][1,4]oxazin-4(4aH)-yl]-2-oxoethyl acetate (Compound No. 06)

Diisopropyl ethylamine (1.68 mL), dimethylamino pyridine (0.35 mL) and acetoxyl acetyl chloride (0.311 mL) was added to the compound tertbutyl 6-{4-[5-(aminomethyl)-2-oxo-1,3-oxazolidin-3-yl]-2-fluorophenyl} hexahydropyrrolo[3,4-b][1,4]oxazine-4(4aH)-carboxylate (1 g) obtained from the above step b Example 03 in dimethyl formamide (10 mL) and stirred for overnight. The reaction mixture was poured in water and extracted with ethyl acetate washed with citric acid and water and dried over anhydrous sodium sulphate, concentrated and purified by column using 2% methanol in dichloromethane as eluant to yield the title compound (790 mg).

$^1$H NMR (DMSO) δ: 8.23 (m, 1H), 7.43-7.37 (dd, 1H), 7.11-7.08 (d, 1H), 6.71 (m, 1H), 4.96-3.39 (m, 17H), 2.09 (s, 3H), 1.83 (s, 3H)

m/z: M+Na=501.43; M+K: 517.40 M+=478

Analogues of 2-[6-(4-{5-[(acetylamino)methyl]-2-oxo-1,3-oxazolidin-3-yl}-2-fluorophenyl)hexahydropyrrolo[3,4-b][1,4]oxazin-4(4aH)-yl]-2-oxoethyl acetate (Compound No. 06) were prepared by replacing acetoxy acetyl chloride with appropriate acylating or sulphonating agents as applicable in each case:

N-[(3-{4-[(7aE)-4-acetylhexahydropyrrolo[3,4-b][1,4]oxazin-6(2H)-yl]-3-fluorophenyl}-2-oxo-1,3-oxazolidin-5-yl)methyl]acetamide (Compound No. 07)

m/z: M+1=421.44; M+Na: 443.42

N-[(3-{4-[(7aE)-4-benzoylhexahydropyrrolo[3,4-b][1,4]oxazin-6(2H)-yl]-3-fluorophenyl}-2-oxo-1,3-oxazolidin-5-yl)methyl]acetamide (Compound No. 08)

m/z: M+1=483.44; M+K=521.42

N-[(3-{3-fluoro-4-[(7aE)-4-(4-fluorobenzoyl)hexahydropyrrolo[3,4-b][1,4]oxazin-6(2H)-yl]phenyl}-2-oxo-1,3-oxazolidin-5-yl)methyl]acetamide (Compound No. 09)

m/z: M+1=501.47, M+Na=523.45 M+K=539.41

N-[(3-{3-fluoro-4-[(7aE)-4-(methylsulfonyl)hexahydropyrrolo [3,4-b][1,4]oxazin-6(2H)-yl]phenyl}-2-oxo-1,3-oxazolidin-5-yl)methyl]acetamide (Compound No. 10)

m/z: M+1: 457.4; M+Na: 479.36; M+K: 495.36

Example 7

Synthesis of N-({3-[3-fluoro-4-(4-glycoloylhexahydropyrrolo[3,4-b][1,4]oxazin-6(2H)-yl)phenyl]-2-oxo-1,3-oxazolidin-5-yl}methyl)acetamide (Compound No. 11)

To the compound 2-[6-(4-{5-[(acetylamino)methyl]-2-oxo-1,3-oxazolidin-3-yl}-2-fluorophenyl)hexahydropyrrolo [3,4-b][1,4]oxazin-4(4aH)-yl]-2-oxoethyl acetate (590 mg) obtained from Example 06 above in methanol (15 ml) was added potassium carbonate (0.34 g) and stirred for overnight. The reaction mixture was filtered, concentrated and purified by column using 3% methanol in dichloromethane as eluant to yield the title compound (300 mg).

$^1$H NMR (CDCl$_3$) δ: 7.34 (m, 1H), 7.02 (d, 1H), 6.59 (m, 1H), 6.0 (bs, 1H), 5.0 (bs, 1H), 4.74-4.73 (m, 1H), 4.26-3.23 (m, 16H), 2.02 (s, 3H).

m/z: M+1=437.51; M+Na=459.49; M+K: 475.44

Example 8

Synthesis of 3-{3-fluoro-4-[(7aE)-hexahydropyrrolo [3,4-b][1,4]oxazin-4(4aH)-yl]phenyl}-5-(iodomethyl)-1,3-oxazolidin-2-one (Compound No. 12)

Step a: Synthesis of tert-butyl (7aE)-hexahydropyrrolo[3,4-b][1,4]oxazine-6(2H)-carboxylate Triethylamine (1 mL) and tertbutyloxy carbonyl anhydride( 5.7 g) was added to the compound (7aE)-octahydropyrrolo[3,4-b][1,4]oxazine (11.5 g) (prepared as per the procedure given in DE4200415) in a mixture of dichloromethane and tetrahydrofuran (11 mL) and stirred for about 2 hrs at 0° C. and overnight at room temperature. The reaction mixture was extracted with dichloromethane. The organic layer was washed with sodium hydrogen carbonate, citric acid and water dried over anhydrous sodium sulphate The mixture was taken in methanol and to it was added palladium hydroxide (4 g) and was hydrogenated for overnight at 50 psi. The reaction mixture was filtered over celite, concentrated to yield the title compound (11.6 g)

Step b: Synthesis of tert-butyl (7aE)-4-(2-fluoro-4-nitrophenyl)hexahydropyrrolo[3,4-b][1,4]oxazine-6 (2H)-carboxylate Potassium carbonate (20.91 g) and 3,4-dinitrobenzene (5.48 mL) were added to the compound (11.5 g) obtained form step a above in dimethyl formamide (60 mL) and refluxed for about 17 hrs at 80° C. The reaction mixture was concentrated and the crude product was taken in water and extracted with dichloromethane. The organic layer were combined and washed with water and brine and dried over sodium sulphate. The compound was triturated with hexane, the organic layer was evaporated and purified by column using 20% ethyl acetate in hexane to furnish the title compound (12.1 g).

Step c: Synthesis of tert-butyl (7aE)-4-(4-amino-2-fluorophenyl)hexahydropyrrolo[3,4-b][1,4]oxazine-6 (2H)-carboxylate Pd/C (3 g, 5%) was added to the compound (12 g) obtained from the step b above in methanol (50 mL) and the reaction mixture was hydrogenated at 50 psi overnight. The reaction mixture was filtered through celite bed and the organic layer was concentrated to get the title compound (10 g).

Step d: Synthesis of tert-butyl (7aE)-4-(4-{allyl [(benzyloxy)carbonyl]amino}-2-fluorophenyl) hexahydropyrrolo[3,4-b][1,4]oxazine-6(2H)-carboxylate Sodium hydrogen carbonate (9.97 g) and benzoyloxy chloride (6.35 mL) were added to the compound (10 g) obtained from the step c above in tetrahydrofuran (150 mL) at 0° C. and the reaction mixture was stirred for about 1.5 hrs. The reaction mixture was filtered and the organic layer was concentrated to tert-butyl 4-(4-{allyl[(benzyloxy)carbonyl] amino}phenyl)hexahydropyrrolo[3,4-b][1,4]oxazine-6(2H)-carboxylate. The compound so obtained (13 g) was taken in tetrahydrofuran (150 mL) and cooled to 0° C. To the reaction mixture was added sodium hydride (0.99 g) and stirred for half an hour, followed by the addition of allyl bromide (3.36 mL) and tetra butyl ammonium iodide (1.3 g) and stirred for about 1 hour at room temperature. The reaction mixture was quenched with ice water and extracted with ethyl acetate. The organic layer was washed with water and brine and dried over anhydrous sodium sulphate and concentrated to yield the title compound (15.3 g).

Step e: Synthesis of 3-{3-fluoro-4-[(7aE)-hexahydropyrrolo[3,4-b][1,4]oxazin-4(4aH)-yl]phenyl}-5-(iodomethyl)-1,3-oxazolidin-2-one (Compound No. 12)

Iodine (21.2 g) was added to the compound (15.2 g) obtained from the step d above in dichloromethane (250 mL) and the reaction mixture was stirred for overnight at room temperature. The reaction mixture was washed with sodium thiosulphate. The organic layer thus separated was washed with water and dried over anhydrous sodium sulphate and concentrated and purified by column using 5% methanol in dichloromethane as eluant to yield the title compound (18.08 g).
$^1$H NMR (CD$_3$CN) δ: 7.54-7.48 (dd, 1H), 7.21 (d, 1H), 7.07 (t, 1H), 4.6 (m, 1H), 4.28-4.27 (m, 2H), 4.13-4.12 (t, 1H), 3.95 (d, 1H), 3.75-3.74 (m, 2H), 3.67-3.66 (m, 2H), 3.51 (m, 4H), 3.38 (m, 1H), 2.97-2.93 (dd, 1H).
m/z: M+1=448.30; M+Na; 470.29; M+K=489.33.

Example 9

Synthesis of N-[(3-{3-fluoro-4-[(7aE)-hexahydropyrrolo[3,4-b][1,4]oxazin-4(4aH)-yl]phenyl}-2-oxo-1,3-oxazolidin-5-yl)methyl]acetamide (Compound No. 13)

Step a: Synthesis of 3-{3-fluoro-4-[(7aE)-hexahydropyrrolo[3,4-b][1,4]oxazin-4(4aH)-yl]phenyl}-5-(iodomethyl)-1,3-oxazolidin-2-one Sodium azide (9.48 g) was added to the compound (16 g) obtained form the step e of above Example 08 in dimethyl formamide (200 mL) and the reaction mixture was stirred at 60° C. for about 3 hrs and filtered. The filtrate was concentrated to give the title compound (19.1 g).

Step b: Synthesis of 5-(aminomethyl)-3-{3-fluoro-4-[(7aE)-hexahydropyrrolo[3,4-b][1,4]oxazin-4(4aH)-yl]phenyl}-1,3-oxazolidin-2-one Triphenyl phosphine 0.159 g) was added to the compound (0.165 g) obtained from the step a above in dry tetrahydrofuran (10 mL) and stirred for about 2 hrs. To the reaction mixture was added water (0.052 mL) and was refluxed for about 5 hrs at 40° C. The reaction mixture was concentrated and acidified with 1N hydrochloric acid and extracted with ethyl acetate and water. The aqueous layer was basified and extracted with ethyl acetate and water. The organic layer was dried over anhydrous sodium sulphate and concentrated to give the title compound (100 mg).

Step c: Synthesis of N-[(3-{3-fluoro-4-[(7aE)-hexahydropyrrolo[3,4-b][1,4]oxazin-4(4aH)-yl]phenyl}-2-oxo-1,3-oxazolidin-5-yl)methyl]acetamide (RBx-11430) (Compound No. 13)

Pyridine (0.18 mL) was added to the compound (0.1 g) obtained form the step b above in dichloromethane (10 mL) at 0° C., and stirred for 10 minutes followed by the addition of acetic anhydride (0.108 mL) and further stirred for 2 hrs. The reaction mixture was poured in water and treated with 1 N hydrochloric acid, extracted with dichloromethane. The organic layer was washed with sodium hydrogen carbonate followed by brine and dried over anhydrous sodium sulphate and concentrated and purified by column using 4% methanol in dichloromethane as eluant to give the title compound (70 mg).
$^1$H NMR (CDCl$_3$) δ: 7.45 (m, 1H), 7.05 (m, 1H), 6.95-6.92 (m, 1H), 6.05 (bs, 1H), 4.76 (m, 1H), 4.19-2.85 (m, 15H), 2.03 (s, 3H) m/z: M+1: 379.32.

Example 10

Synthesis of tert-butyl (7aE)-4-{2-fluoro-4-[5-(iodomethyl)-2-oxo-1,3-oxazolidin-3-yl]phenyl}hexahydropyrrolo[3,4-b][1,4]oxazine-6(2H)-carboxylate (Compound No. 14)

Triethyl amine (8.3 mL), tertbutyloxy carbonyl anhydride (11.86 mL) and dimethylaminopyridine (4.85 g) were added to the compound (17.8 g) obtained from the step b of Example 09 above was taken in a mixture of dichloromethane and tetrahydrofuran (400:20 mL) and stirred of 2 hrs at 0° C. and overnight at room temperature. The reaction mixture was extracted with dichloromethane. The organic layer was washed with sodium hydrogen carbonate, citric acid and water dried over anhydrous sodium sulphate and concentrated to get the title compound (16.4 g)
$^1$H NMR (DMSO) δ: 7.55-7.49 (dd, 1H), 7.21-7.09 (m, 2H), 4.72 (m, 1H), 4.17-2.5 (m, 14H), 1.38 (s, 9H).
m/z: M-Boc 448.27, M+Na:570.29, M+1: 548.30.

Example 11

Synthesis of tert-butyl (7aE)-4-(4-{5-[(acetylamino)methyl]-2-oxo-1,3-oxazolidin-3-yl}-2-fluorophenyl)hexahydropyrrolo[3,4-b][1,4]oxazine-6(2H)-carboxylate (Compound No. 15)

Step a: Synthesis of tert-butyl (7aE)-4-{4-[5-(azidomethyl)-2-oxo-1,3-oxazolidin-3-yl]-2-fluorophenyl}hexahydropyrrolo[3,4-b][1,4]oxazine-6(2H)-carboxylate Sodium azide (9.48 g) was added to the compound (16 g) obtained form the above Example 10 in dimethyl formamide (200 mL) and the reaction mixture was stirred at 60° C. for 3 hrs. The reaction mixture was filtered and the filtrate was concentrated to give the title compound (19.1 g).

Step b: Synthesis of tert-butyl (7aE)-4-{4-[5-(aminomethyl)-2-oxo-1,3-oxazolidin-3-yl]-2-fluorophenyl}hexahydropyrrolo[3,4-b][1,4]oxazine-6(2H)-carboxylate Triphenyl phosphine (18.337 g) was added to the compound (1 g) obtained from the step a above in dry tetrahydrofuran (300 mL) and the reaction mixture was stirred for 2 hrs. To the reaction mixture was added water and was further refluxed for 5 hrs at 40° C. The reaction mixture was concentrated and acidified with 1N hydrochloric acid and extracted with ethyl acetate and water. The aqueous layer was basified with 1N sodium hydroxide and extracted with ethyl acetate and water. The organic layer was dried over anhydrous sodium sulphate and concentrated to give the title compound. (9.5 g)

Step c: Synthesis of tert-butyl (7aE)-4-(4-{5-[(acety-lamino)methyl]-2-oxo-1,3-oxazolidin-3-yl}-2-fluorophenyl)hexahydropyrrolo[3,4-b][1,4]oxazine-6 (2H)-carboxylate (Compound No. 15)

Triethylamine (2.15 mL) was added to the compound (4.8 g) obtained form the step b above in dichloromethane (100 mL) at 0° C., and stirred for 10 minutes followed by the addition of acetic anhydride (1.17 mL) and stirred further for 2 hrs. The reaction mixture was poured in water and extracted with dichloromethane. The organic layer was given a wash with sodium hydrogen carbonate followed by brine and dried over anhydrous sodium sulphate and concentrated and purified by column using 2% methanol in dichloromethane as eluant to furnish the title compound (2.5 g).

$^1$H NMR (CDCl$_3$) δ: 7.26 (m, 1H), 6.93 (m, 2H), 6.0 (bs, 1H), 4.77-4.76 (m, 1H), 4.18-3.41 (m, 14H), 2.02 (s, 3H), 1.33 (s, 9H).

m/z: M-Boc: 379.27, M+Na:501.29.

Example 12

Synthesis of 2-[(7aE)-4-(4-{5-[(acetylamino)methyl]-2-oxo-1,3-oxazolidin-3-yl}-2-fluorophenyl) hexahydropyrrolo[3,4-b][1,4]oxazin-6(2H)-yl]-2-oxoethyl acetate (Compound No. 16)

Ethanolic hydrochloride (10 mL) was added to the compound (200 mg) obtained from the step c, of Example 11 and the reaction mixture was stirred for 2 hrs at 0° C. and the solvent was distilled off. The crude was taken in dimethyl formamide (10 mL), diisopropylethylamine (0.29 mL), dimethyl aminopyridine (0.062 g) and acetoxyacetyl chloride (0.0539 mL) and the reaction mixture was stirred overnight. The reaction mixture was poured in water and extracted with ethyl acetate washed with citric acid and water and dried over anhydrous sodium sulphate, concentrated and purified by column using 5% methanol in dichloromethane as eluant to yield the title compound (50 mg).

$^1$H NMR (CDCl$_3$) δ:7.49-7.43 (m, 1H), 7.1 (m, 1H), 6.97-6.91 (m, 1H), 6.01 (m, 1H), 4.55 (m, 1H), 4.02-3.46 (m, 16H), 2.16-2.15 (S, 3H), 2.02 (S, 3H).

m/z: 478.47; M+23: 501.25; M-CH$_3$CO=437.28.

Analogues of 2-[(7aE)-4-(4-{5-[(acetylamino)methyl]-2-oxo-1,3-oxazolidin-3-yl}-2-fluorophenyl)hexahydropyrrolo[3,4-b][1,4]oxazin-6(2H)-yl]-2-oxoethyl acetate (Compound No. 16), were prepared by replacing acetoxy acetylchloride with appropriate acylating or sulphonating agents as applicable in each case:

N-[(3-{4-[(7aE)-6-benzoylhexahydropyrrolo[3,4-b][1,4]oxazin-4(4aH)-yl]-3-fluorophenyl}-2-oxo-1,3-oxazolidin-5-yl)methyl]acetamide (Compound No. 17)

m/z: M+1=483.27; M+Na: 505.26

N-[(3-{4-[(7aE)-6-acetylhexahydropyrrolo[3,4-b][1,4]oxazin-4(4aH)-yl]-3-fluorophenyl}-2-oxo-1,3-oxazolidin-5-yl)methyl]acetamide (Compound No. 18)

m/z: 420.44; M+1:421.24; M+23:479.23

N-[(3-{3-fluoro-4-[(7aE)-6-(methylsulfonyl)hexahydropyrrolo[3,4-b][1,4]oxazin-4(4aH)-yl]phenyl}-2-oxo-1,3-oxazolidin-5-yl)methyl]acetamide (Compound No. 19)

m/z: M-COCH$_3$: 415.19, M+1=457.27; M+23: 479.23

Example 13

Synthesis of N-[(3-{3-fluoro-4-[(7aE)-6-glycoloylhexahydropyrrolo[3,4-b][1,4]oxazin-4(4aH)-yl]phenyl}-2-oxo-1,3-oxazolidin-5-yl)methyl]acetamide (Compound No. 20)

Potassium carbonate (0.28 g) was added to the compound (500 mg) obtained from Example 12 above in methanol (15 mL) and stirred for overnight. The reaction mixture was filtered, concentrated and purified by column using 2.5% methanol in dichloromethane as eluant to yield the title compound (60 mg).

$^1$H NMR CDCl$_3$ δ: 7.46 (t, 1H), 6.97 (m, 2H), 6.04 (bs, 1H), 4.77-4.76 (m, 1H), 4.28-2.91 (m, 17H), 2.02 (s, 3H)

m/z: M+1=437.23; M-OH=421.24; M+23: 459.23.

Assay for in vitro Antibacterial Activity

The compounds of the invention display antibacterial activity when tested by the agar incorporation method. The following minimum inhibitory concentrations (μg/mL) were obtained for representative compound of the invention, which is given below in the following table.

Guide to Table Abbreviations:

S. aureus ATCC 25923—*Staphylococcus aureus* ATCC 25923; S. aureus ATCC 15187—*Staphylococcus aureus* ATCC 15187; MRSA—Methicilline Resistant *Staphylococcus aureus* ATCC562; MRSA—Methicilline Resistant *Staphylococcus aureus* ATCC33; Ent. faecalis ATCC 29212—*Enterococcus faecalis* ATCC 29212; Strep. pyog. ATCC 19615—*Streptococcus pyogenes*; S. pneum ATCC6303—*Streptococcus pneumonia* ATCC6303; S. pneum ATCC AB34—*Streptococcus pneumonia* ATCC AB34; M. catt.—*Moraxella catarrhalis* ATCC 8176; VRE—Vancomycin-resistant enterococci ATCC 6A; H. influ.—*Haemophilus influenzae*

TABLE 1

| Compound No. | S. aureus 25923 | S. aureus 15187 | MRSA 562 | MRSA 33 | E. faecalis 29212 | VRE 6A | S. pyogenes 19615 | S. pneum 6303 | S. pneum AB34 | M. catt 8176 | H. inf 49247 |
|---|---|---|---|---|---|---|---|---|---|---|---|
| Linezolid | 2 | 2 | 2 | 2 | 2 | 2 | 2 | 1 | 2 | 2 | 8 |
| 05 | 8 | 8 | 4 | 4 | 2 | 2 | 2 | 2 | 2 | >16 | 8 |

The in vitro antibacterial activity of the compounds was demonstrated by the agar dilution method (NCCLS M 7-A5 and M 100-S8 documents). Briefly, the compounds were dissolved in dimethylsulphoxide and doubling dilution of the compounds was incorporated into Muller Hilton agar before solidification. Inoculum for *staphylococcus aureus* and *Enterococus* strain was prepared by direct colony suspension in normal saline solution and adjusting the turbidity to 0.5 Macfarland turbidity and subsequently diluting as per NCCLS guidelines in order to obtain $10^4$ CFU/spot. CFU/mL of few randomly selected cultures was performed. The cultures were replicated on agar plate using Denley's multipoint replicator. The agar plates were incubated for 18 hours-24 hours (24 hours for MRSA studies) at 35±2° C. Q.C. strains were also included in each run of the study.

The in vitro activity for *Haemophilus* MICs were performed by using Microbroth dilution method as follows:

Media used: Mueller Hinton Broth (MHB-Difco)–
Cation adjusted+5 grams per liter Yeast extract+
supplements Preparation of drug concentrations in 96 well microtitre plates were done as per the NCCLS method. Inoculum was prepared by direct colony suspensions in normal saline and adjusted to 1 McFarland turbidity and subsequently diluted in broth 100 times as per NCCLS guidelines in order to obtain $10^5$ CFU/spot.

Inoculum preparation for *Streptococcus pneumoniae, Moraxella catarrhalis, Streptococcus pyogenes* strains and the method of MIC is an agar dilution method with MHA (Mueller Hinton agar) and 5% sheep blood. Inoculum was prepared by direct colony suspension in normal saline solution and adjusting the turbidity to 1 Mcfarland and subsequently diluting as per NCCLS guidelines in order to obtain $10^4$ CFU/ml. The plates were incubated in $CO_2$ at 37° C. for 18-24 hours.

The concentration showing no growth of the inoculated culture was recorded as the MIC. Appropriate ATCC standard strains were simultaneously tested and result recorded only when the MIC's against standard antibiotics were within the acceptable range.

We Claim:

1. A compound of Formula I,

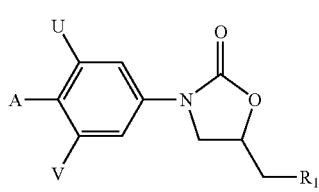

Formula I and their pharmaceutically acceptable salts, pharmaceutically acceptable esters, enantiomers, diastereomers, or N-oxides, wherein U and V are selected from hydrogen and fluorine (wherein both U and V cannot simultaneously be hydrogen);

A is selected from;

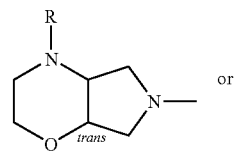

Formula A or

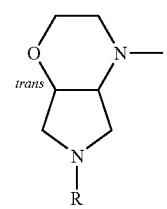

Formula B

R is H, alkyl, alkenyl, alkynyl, alkoxy, cycloalkyl, aryl, aralkyl, heteroaryl, heterocyclyl, heteroarylalkyl or heterocyclylalkyl, —$COR_a$, —$C(O)OR_a$, or $S(O)_2R_a$;

$R_1$ is azido, halogen, NCS, $NHYR_jNR_jC(=T)NR_jR_q$, $NR_jR_q$ or $NR_j(C=O)OR_s($ );

$R_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or $SO_2$;

$R_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —$N(NO_2)$, or —$CH(NO_2)$;

$R_j$ is hydrogen, alkyl, alkenyl, cycloalkyl, aryl, aralkyl, heterocyclyl, heteroaryl, heteroarylalkyl or heterocyclylalkyl;

$R_q$ is hydrogen, alkyl, cycloalkyl, aryl, aralkyl, heteroaryl, heterocyclyl, heteroarylalkyl or heterocyclylalkyl, and $R_s$ is alkyl, alkenyl, alkynyl, cycloalkyl, aryl, aralkyl, heteroarylalkyl or heterocyclylalkyl.

2. A compound selected from:

3-{3-fluoro-4-[(7aE)-hexahydropyrrolo[3,4-b][1,4]oxazin-4(4aH)-yl]phenyl}-5-(iodomethyl)-1,3-oxazolidin-2-one;

tert-butyl (7aE)-6-{2-fluoro-4-[5-(iodomethyl)-2-oxo-1,3-oxazolidin-3-yl]phenyl}hexahydropyrrolo[3,4-b][1,4]oxazine-4(4aH)-carboxylate;

tert-butyl (7aE)-6-{4-[5-(aminomethyl)-2-oxo-1,3-oxazolidin-3-yl]-2-fluorophenyl}hexahydropyrrolo[3,4-b][1,4]oxazine-4(4aH)-carboxylate;

tert-butyl (7aE)-6-(4-{5-[(acetylamino)methyl]-2-oxo-1,3-oxazolidin-3-yl}-2-fluorophenyl)hexahydropyrrolo[3,4-b][1,4]oxazine-4(4aH)-carboxylate;

N-[(3-{3-fluoro-4-[(7aE)-hexahydropyrrolo[3,4-b][1,4] oxazin-6(2H)-yl]phenyl}-2-oxo-1,3-oxazolidin-5-yl)methyl]acetamide;

2-[(7aE)-6-(4-{5-[(acetylamino)methyl]-2-oxo-1,3-oxazolidin-3-yl}-2-fluorophenyl)hexahydropyrrolo[3,4-b][1,4]oxazin-4(4aH)-yl]-2-oxoethyl acetate;

N-[(3-{4-[(7aE)-4-acetylhexahydropyrrolo[3,4-b][1,4] oxazin-6(2H)-yl]-3-fluorophenyl}-2-oxo-1,3-oxazolidin-5-yl)methyl]acetamide;

N-[(3-{4-[(7aE)-4-benzoylhexahydropyrrolo[3,4-b][1,4] oxazin-6(2H)-yl]-3-fluorophenyl}-2-oxo-1,3-oxazolidin-5-yl)methyl]acetamide;

N-[(3-{3-fluoro-4-[(7aE)-4-(4-fluorobenzoyl)hexahydropyrrolo[3,4-b][1,4]oxazin-6(2H)-yl]phenyl}-2-oxo-1,3-oxazolidin-5-yl)methyl]acetamide;

N-[(3-{3-fluoro-4-[(7aE)-4-(methylsulfonyl)hexahydropyrrolo[3,4-b][1,4]oxazin-6(2H)-yl]phenyl}-2-oxo-1,3-oxazolidin-5-yl)methyl]acetamide;

N-[(3-{3-fluoro-4-[(7aE)-4-glycoloylhexahydropyrrolo[3,4-b][1,4]oxazin-6(2H)-yl]phenyl}-2-oxo-1,3-oxazolidin-5-yl)methyl]acetamide;

3-{3-fluoro-4-[(7aE)-hexahydropyrrolo[3,4-b][1,4]oxazin-4(4aH)-yl]phenyl}-5-(iodomethyl)-1,3-oxazolidin-2-one;

N-[(3-{3-fluoro-4-[(7aE)-hexahydropyrrolo[3,4-b][1,4] oxazin-4(4aH)-yl]phenyl}-2-oxo-1,3-oxazolidin-5-yl)methyl]acetamide;

tert-butyl (7aE)-4-{2-fluoro-4-[5-(iodomethyl)-2-oxo-1,3-oxazolidin-3-yl]phenyl}hexahydropyrrolo[3,4-b][1,4]oxazine-6(2H)-carboxylate;

tert-butyl (7aE)-4-(4-{5-[(acetylamino)methyl]-2-oxo-1,3-oxazolidin-3-yl}-2-fluorophenyl)hexahydropyrrolo[3,4-b][1,4]oxazine-6(2H)-carboxylate;

2-[(7aE)-4-(4-{5-[(acetylamino)methyl]-2-oxo-1,3-oxazolidin-3-yl}-2-fluorophenyl)hexahydropyrrolo[3,4-b][1,4]oxazin-6(2H)-yl]-2-oxoethyl acetate;

N-[(3-{4-[(7aE)-6-benzoylhexahydropyrrolo[3,4-b][1,4] oxazin-4(4aH)-yl]-3-fluorophenyl}-2-oxo-1,3-oxazolidin-5-yl)methyl]acetamide;

N-[(3-{4-[(7aE)-6-acetylhexahydropyrrolo[3,4-b][1,4] oxazin-4(4aH)-yl]-3-fluorophenyl}-2-oxo-1,3-oxazolidin-5-yl)methyl]acetamide;

N-[(3-{3-fluoro-4-[(7aE)-6-(methylsulfonyl)hexahydropyrrolo[3,4-b][1,4]oxazin-4(4aH)-yl]phenyl}-2-oxo-1,3-oxazolidin-5-yl)methyl]acetamide; and N-[(3-{3-fluoro-4-[(7aE)-6-glycoloylhexahydropyrrolo[3,4-b][1,4]oxazin-4(4aH)-yl]phenyl}-2-oxo-1,3-oxazolidin-5-yl)methyl]acetamide.

3. A pharmaceutical composition comprising a therapeutically effective amount of compound of Formula I

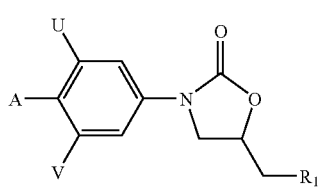

Formula I or pharmaceutically acceptable salts, pharmaceutically acceptable, enantiomers, diastereomers, and one or more pharmaceutical acceptable carrier, wherein U and V are selected from hydrogen and fluorine (wherein both U and V cannot simultaneously be hydrogen);

A is selected from

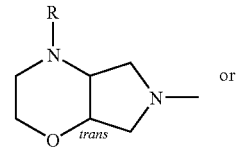

Formula A or

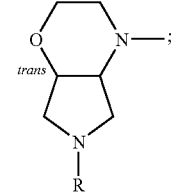

Formula B

R is H, alkyl, alkenyl, alkynyl, alkoxy, cycloalkyl, aryl, aralkyl, heteroaryl, heterocyclyl, heteroarylalkyl or heterocyclylalkyl, —COR$_a$, —C(O)OR$_a$, or S(O)$_2$R$_a$;

R$_1$ is azido, halogen, NCS, NHYR$_f$NR$_j$C(=T)NR$_j$R$_q$, NR$_j$R$_q$ or NR$_j$(C=O)OR$_s$( );

R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or SO$_2$;

R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —N(NO$_2$), or —CH(NO$_2$);

R$_j$ is hydrogen, alkyl, alkenyl, cycloalkyl, aryl, aralkyl, heterocyclyl, heteroaryl, heteroarylalkyl or heterocyclylalkyl;

R$_q$ is hydrogen, alkyl, cycloalkyl, aryl, aralkyl, heteroaryl, heterocyclyl, heteroarylalkyl or heterocyclylalkyl, and R$_s$ is alkyl, alkenyl, alkynyl, cycloalkyl, aryl, aralkyl, heteroarylalkyl or heterocyclylalkyl.

4. A method of treating microbial infections in a mammal, wherein the microbial infections are caused by gram-positive and gram-negative bacteria, comprising administering to a mammal in need thereof a therapeutically effective amount of a compound of Formula I

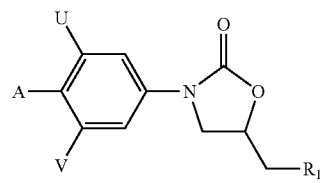

Formula I or its pharmaceutically acceptable salts, pharmaceutically acceptable enantiomers, or diastereomers, wherein U and V are selected from hydrogen and fluorine (wherein both U and V cannot simultaneously be hydrogen);

A is selected from

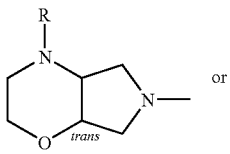

Formula A or

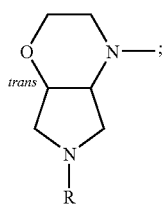

Formula B

R is H, alkyl, alkenyl, alkynyl, alkoxy, cycloalkyl, aryl, aralkyl, heteroaryl, heterocyclyl, heteroarylalkyl or heterocyclylalkyl, —COR$_a$, —C(O)OR$_a$, or S(O)$_2$R$_a$;

R$_1$ is azido, halogen, NCS, NHYR$_f$NR$_j$C(=T)NR$_j$R$_q$, NR$_j$R$_q$ or NR$_j$(C=O)OR$_s$( );

R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or SO$_2$;

R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —N(NO$_2$), —CH(NO$_2$);

R$_j$ is hydrogen, alkyl, alkenyl, cycloalkyl, aryl, aralkyl, heterocyclyl, heteroaryl, heteroarylalkyl or heterocyclylalkyl;

R$_q$ is hydrogen, alkyl, cycloalkyl, aryl, aralkyl, heteroaryl, heterocyclyl, heteroarylalkyl or heterocyclylalkyl, and R$_s$ is alkyl, alkenyl, alkynyl, cycloalkyl, aryl, aralkyl, heteroarylalkyl or heterocyclylalkyl.

5. The method of claim 4, wherein the gram-positive bacteria are selected from *Staphylococcus* spp., *Streptococcus* spp., *Bacillus* spp., *Corynebacterum* spp., *Clostridia* spp., *Peptostreptococus* spp., *Listeria* spp. or *Legionella* spp.

6. A method of treating aerobic and anaerobic bacterial infections comprising administering to a mammal in need thereof a therapeutically effective amount of a compound of Formula I

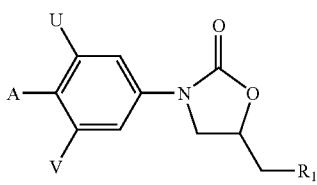

Formula I or its pharmaceutically acceptable salts, pharmaceutically acceptable, enantiomers, or diastereomers, wherein U and V are selected from hydrogen and fluorine (wherein both U and V cannot simultaneously be hydrogen);

A is selected from

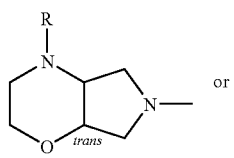

Formula A or

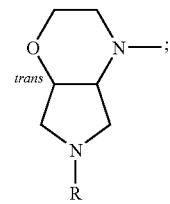

Formula B

R is H, alkyl, alkenyl, alkynyl, alkoxy, cycloalkyl, aryl, aralkyl, heteroaryl, heterocyclyl, heteroarylalkyl or heterocyclylalkyl, —COR$_a$, —C(O)OR$_a$, or S(O)$_2$R$_a$;

R$_1$ is azido, halogen, NCS, NHYR$_f$NR$_j$C(=T)NR$_j$R$_q$, NR$_j$R$_q$ or NR$_j$(C=O)OR$_s$( );

R$_a$ is selected from hydrogen, straight or branched unsubstituted or substituted alkyl, alkenyl, alkynyl, alkoxy, cycloalkyl, aryl, aralkyl, heteroaryl, heterocyclyl, heteroarylalkyl or heterocyclylalkyl;

Y is (C=O), (C=S) or SO$_2$;

R$_f$ is hydrogen, alkyl, alkenyl, alkynyl, alkoxy, cycloalkyl, aryl, aralkyl, heteroaryl, heterocyclyl, heteroarylalkyl or heterocyclylalkyl;

T is O, S, —N(CN), —N(NO$_2$), or —CH(NO$_2$);

R$_j$ is hydrogen, alkyl, alkenyl, cycloalkyl, aryl, aralkyl, heterocyclyl, heteroaryl, heteroarylalkyl or heterocyclylalkyl;

R$_q$ is hydrogen, alkyl, cycloalkyl, aryl, aralkyl, heteroaryl, heterocyclyl, heteroarylalkyl or heterocyclylalkyl, and R$_s$ is alkyl, alkenyl, alkynyl, cycloalkyl, aryl, aralkyl, heteroarylalkyl or heterocyclylalkyl.

7. A process for preparing a compound of Formula VII, VIII, X, XI, XII, XIII and XIIIa,

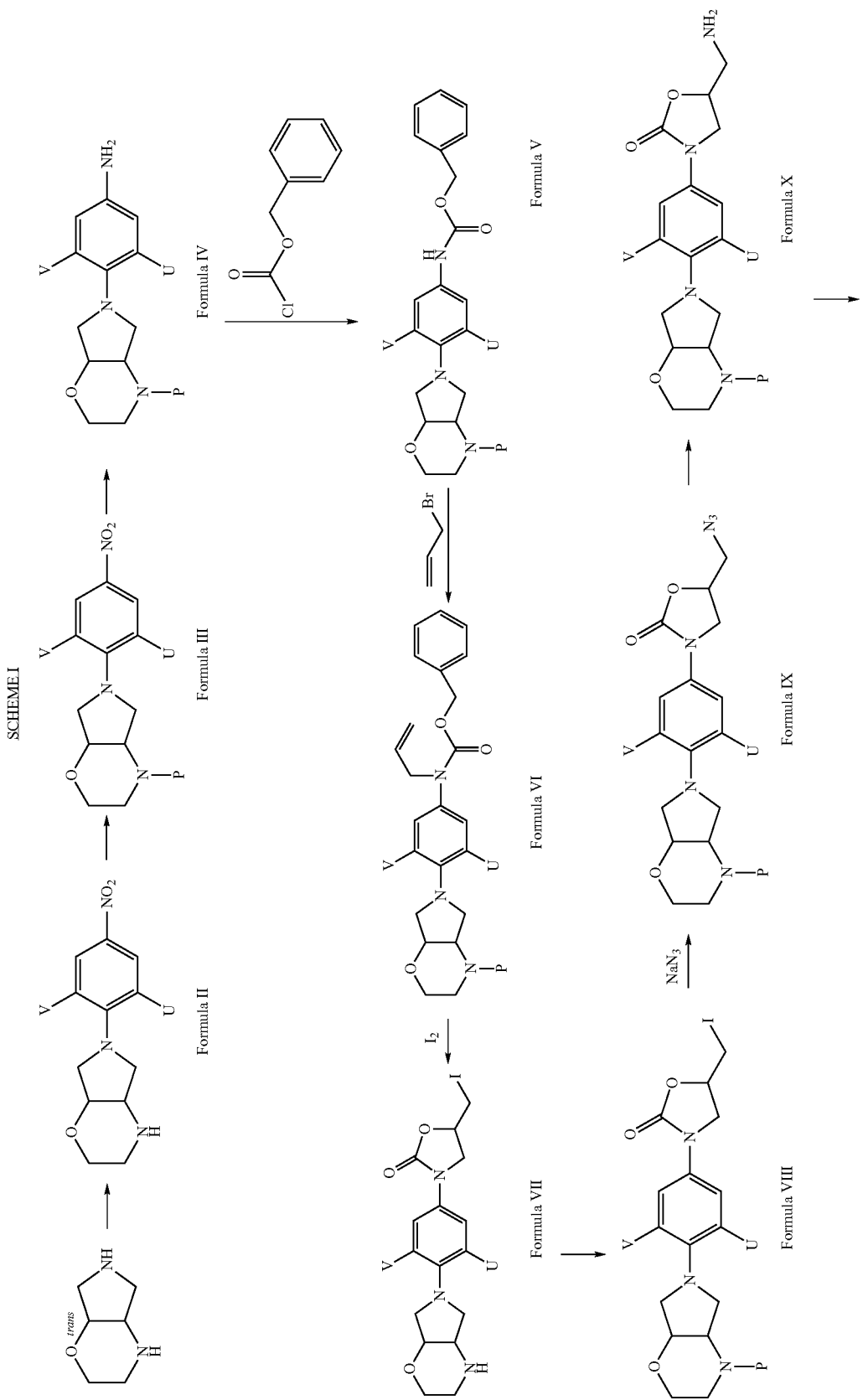

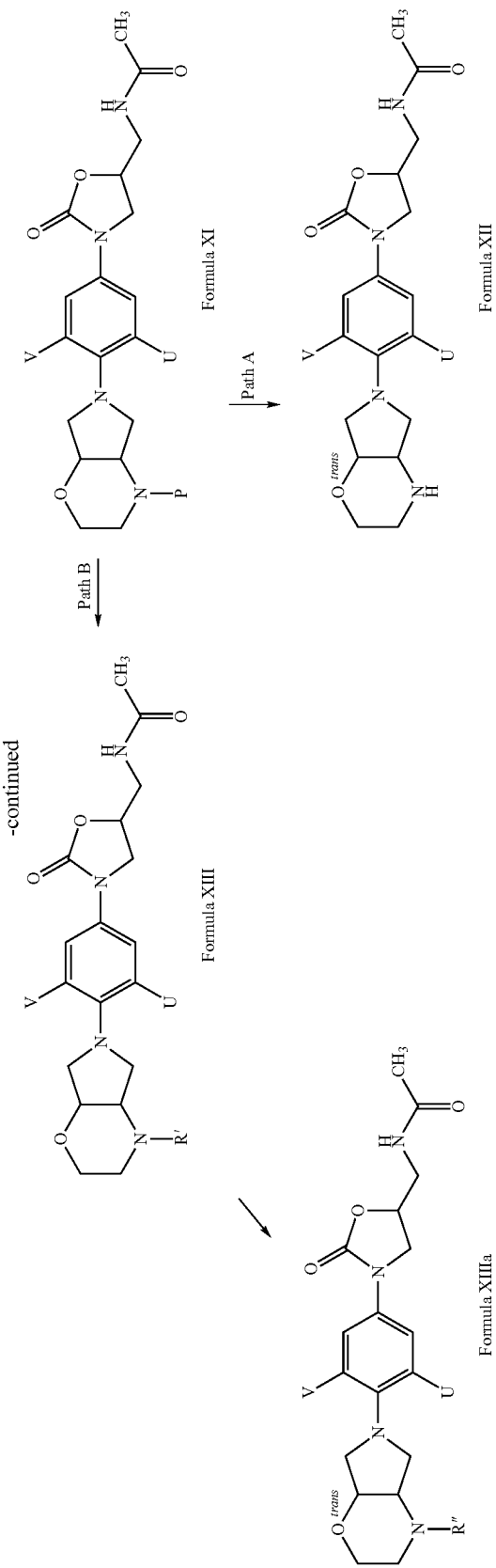

comprising:
reacting compound (7aE)-octahydropyrrolo[3,4-b][1,4]oxazine with substituted nitrobenzene to give the compound of Formula II in a solvent in the presence of a base;
protecting the compound of Formula II with a protecting agent to give a compound of Formula III in the presence of solvent in the presence of a base;
reducing the compound of Formula III to give a compound of Formula IV in a solvent in the presence of a reducing agent;
reacting the compound of Formula IV with benzyloxy carbonyl chloride to give the compound of Formula V in a solvent in the presence of a base;
reacting compound of Formula V with allyl bromide to give a compound of Formula VI in the presence of a base and a phase transfer catalyst;
Cyclising the compound of Formula VI to give the compound of Formula VII in a solvent in the presence of iodine;
protecting the compound of Formula VII with a protecting agent to give compound of Formula VIII in solvent in the presence of a base along with a catalyst;
reacting the compound of Formula VIII with sodium azide or potassium azide to give a compound of Formula IX in solvent;
reducing the compound of Formula IX or diphenylphosphine to give the compound of Formula X;
reacting the compound of Formula X with a acylating agent to give a compound of Formula XI in solvent in the presence of a base;
  Path A: hydrolyzing the compound of Formula XI to give a compound of Formula XII in presence of hydrochloric acid;
  Path B: reacting the compound of Formula XI with an acylating agent or sulphonating agent to give the compound of Formula XIII in solvent, in the presence of a base and a catalyst; and
reacting the compound of Formula XIII to give the compound of Formula XIIIa in the presence of a base.

8. A process for preparing a compound of Formula XVIII, XXI, XXII, XXIII, XXVI and XXVIa

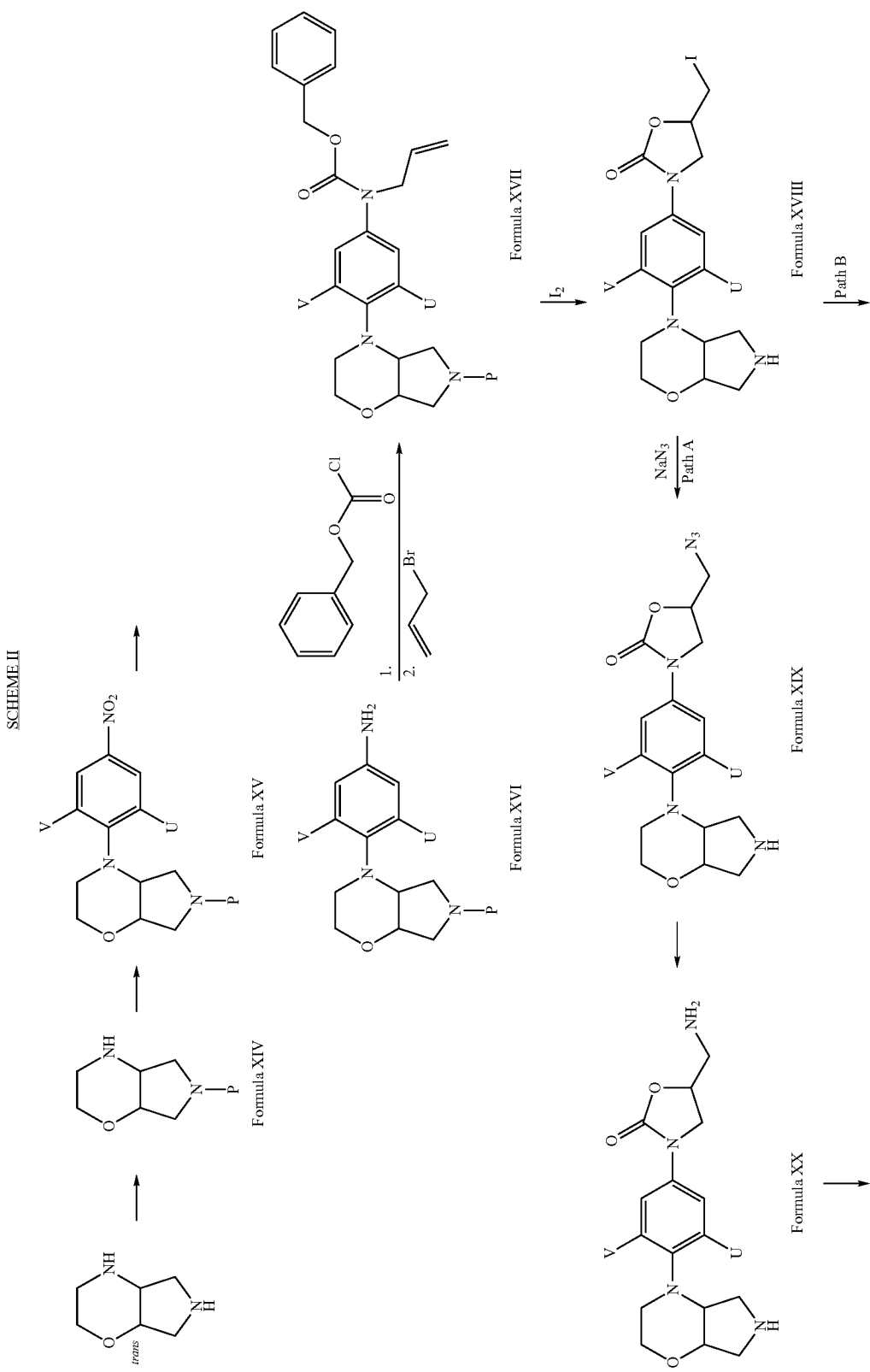

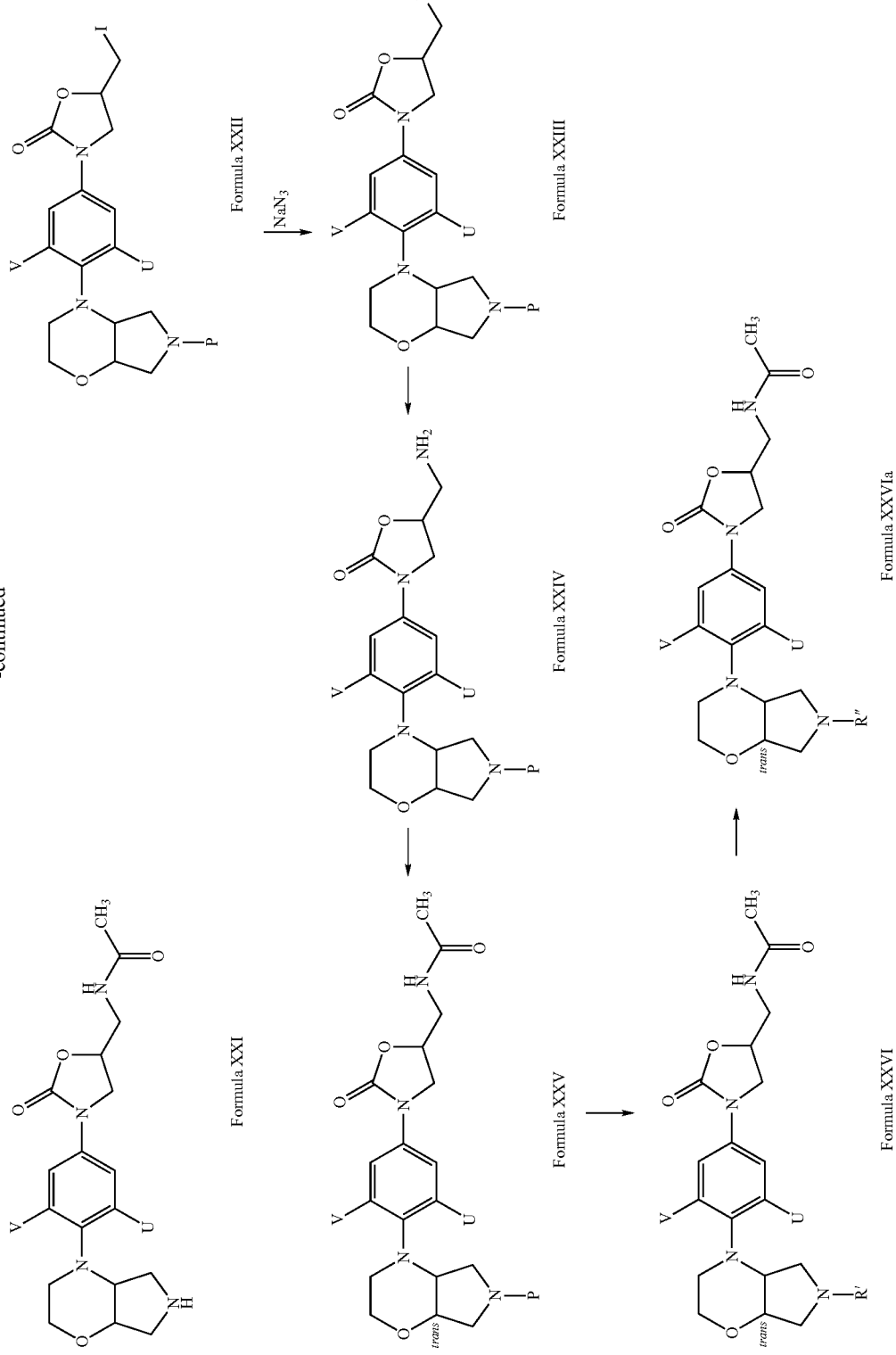

comprising:

protecting the compound (7aE)-octahydropyrrolo[3,4-b][1,4]oxazine with protecting to give compound of Formula XIV in solvent in the presence of a base.

reacting the compound of Formula XIV with substituted nitrobenzene to give a compound of Formula XV in a solvent in the presence of a base;

reducing the compound of Formula XV to give a compound of Formula XVI in a solvent with a reducing agent;

reacting the compound of Formula XVI benzyloxy carbonyl chloride to give the compound of Formula XVII in a in the presence of base which is further reacted with allyl bromide in presence of a solvent or in the presence of a phase transfer catalyst along with a base;

Cyclizing the compound of Formula XVII to give the compound of Formula XVIII in a solvent in the presence of iodine;

Path A: reacting the compound of Formula XVIII whit sodium azide to give a compound of Formula XIX in a solvent; Reducing the compound of Formula XIX in the presence of a catalyst to give the compound of Formula XX in a solvent; Reacting the compound of Formula XX with an acylating agent in a solvent in the presence of a base along with a catalyst to give a compound of Formula XXI;

Path B: Protecting the compound of Formula XVIII with protecting agent to give a compound of Formula XXII in solvent in the presence of a base along with a catalyst; Reacting the compound of Formula XXII with sodium azide or potassium azide to give a compound of Formula XXIII in a solvent; Reducing the compound of Formula XXIII with triphenylphosphine and diphenylphosphine to give the compound of Formula XXIV in a solvent; Reacting the compound of Formula XXIV with an acylating agent to give the compound of Formula XXV in solvent in the presence of a base;

Deprotecting the compound of Formula XXV in ethanloic hydrochloride and reacting with an acylating or sulphonating agent to give the compound of Formula XXVI in solvent in the presence of a base with a catalyst; and reacting the compound of Formula XIII to give the compound of Formula XIIIa with methanol and ethanol in the presence of a base.

* * * * *